(12) United States Patent
Cremer et al.

(10) Patent No.: US 9,517,009 B2
(45) Date of Patent: Dec. 13, 2016

(54) STRUCTURED ILLUMINATION OPHTHALMOSCOPE

(71) Applicants: Universität Heidelberg, Heidelberg (DE); Friedrich-Schiller-Universität Jena, Jena (DE)

(72) Inventors: Christoph Cremer, Heidelberg (DE); Gerrit Best, Heidelberg (DE); Roman Amberger, Bad Reichenhall (DE); Rainer Heintzmann, Jena (DE); Stefan Dithmar, Dossenheim (DE); Thomas Ach, Scharzhofen (DE)

(73) Assignees: Ruprecht-Karls-Universität Heidelberg, Heidelberg (DE); Friedrich-Schiller-Universität Jena, Jena (DE)

( * ) Notice: Subject to any disclaimer, the term of this patent is extended or adjusted under 35 U.S.C. 154(b) by 4 days.

(21) Appl. No.: 14/432,096

(22) PCT Filed: Sep. 26, 2013

(86) PCT No.: PCT/EP2013/002895
§ 371 (c)(1),
(2) Date: Mar. 27, 2015

(87) PCT Pub. No.: WO2014/048570
PCT Pub. Date: Apr. 3, 2014

(65) Prior Publication Data
US 2015/0297076 A1    Oct. 22, 2015

(30) Foreign Application Priority Data

Sep. 28, 2012  (EP) .................................. 12006779

(51) Int. Cl.
*A61B 3/14* (2006.01)
*A61B 3/12* (2006.01)
*A61B 3/00* (2006.01)

(52) U.S. Cl.
CPC ............... *A61B 3/12* (2013.01); *A61B 3/0008* (2013.01)

(58) Field of Classification Search
CPC ............. A61B 3/14; A61B 3/12; A61B 3/102
(Continued)

(56) References Cited

U.S. PATENT DOCUMENTS

2015/0131050 A1* 5/2015 Bublitz .................... A61B 3/12
351/206

FOREIGN PATENT DOCUMENTS

DE       102005034332 A1    1/2007
EP             1992276 A1   11/2008
(Continued)

OTHER PUBLICATIONS

R. Heintzmann et al: "Axial tomographic confocal fluorescence microscopy", Journal of Microscopy, vol. 206, No. 1, Apr. 1, 2002, pp. 7-23.
(Continued)

*Primary Examiner* — Hung Dang
(74) *Attorney, Agent, or Firm* — Armstrong Teasdale LLP

(57) ABSTRACT

A method for non-invasive observations of a fundus using an ophthalmoscope is provided. The method includes illuminating a retinal region of an eye by projecting an illumination pattern of illumination light onto the retinal region, at least one of detecting a portion of fluorescent light emitted from the retinal region and detecting a portion of illumination light reflected from the retinal region, thereby capturing a series of images of the retinal region at a plurality of different relative positions of the retinal region with respect
(Continued)

to the illumination pattern projected onto the retinal region, wherein between the capturing of at least two images of the series the relative position of the retinal region with respect to the illumination pattern projected onto the retinal region is shifted in a non-controlled manner, and processing the captured images to extract a sub-resolution image of the retinal region.

19 Claims, 7 Drawing Sheets

(58) Field of Classification Search
USPC ................................ 351/206, 246, 221, 205
See application file for complete search history.

(56) References Cited

FOREIGN PATENT DOCUMENTS

| WO | 2008124832 A1 | 10/2008 |
|---|---|---|
| WO | 2012059564 A1 | 5/2012 |

OTHER PUBLICATIONS

WO/ISR, PCT/EP2013/002895 filed Sep. 26, 2013, mailed Jul. 16, 2014, Universitat Heidelberg, 21 pages.

G. Best et al., "Structured illumination microscopy of autofluorescent aggregations in human tissue", published in Micron (2010).

R. Heintzmann et al., "Laterally modulated excitation microscopy: Improvement of resolution by using a diffraction grating", proceedings of SPIE (1999), 3568, 185.

\* cited by examiner

SMI
FIG. 3A
conventional

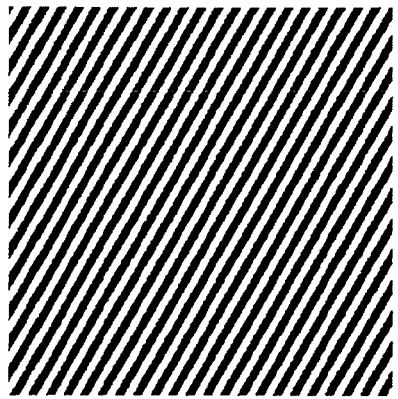
FIG. 6A
unshifted object ρ₀(x)
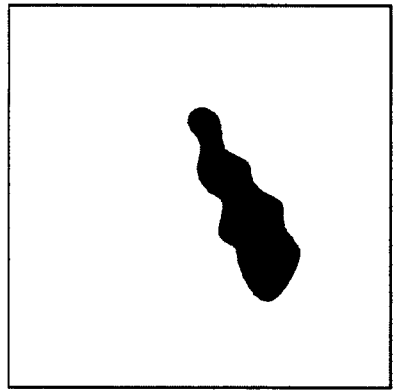
FIG. 6B
shifted object ρ₁(x)
FIG. 6C
illumination pattern $I_{illu}(x)$
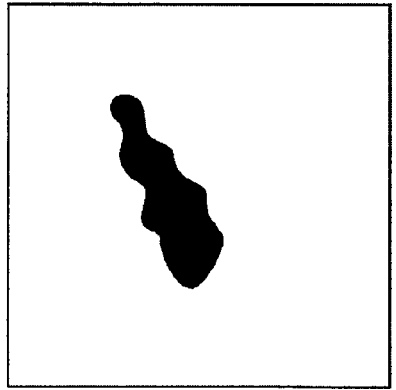
FIG. 6D
Image of illuminated unshifted object $I_{m0}(x)$
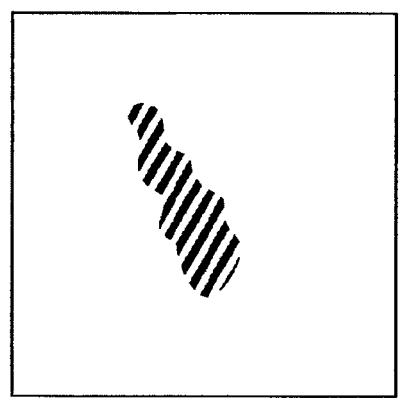
FIG. 6E
Image of illuminated shifted object $I_{m1}(x)$
FIG. 6F
peak in R(x)

STRUCTURED ILLUMINATION OPHTHALMOSCOPE

CROSS REFERENCE TO RELATED APPLICATIONS

This application is a National Stage Entry of PCT/EP2013/002895 filed Sep. 26, 2013, which claims priority from European Patent Application No. EP 12006779.8 filed Sep. 28, 2012, both of which are incorporated herein in their entirety.

BACKGROUND

The present invention relates to a high resolution microscopy for the use in ophthalmology.

In particular, the present invention relates to a method, an apparatus (an ophthalmoscope), a computer implemented method and a computer program product for non-invasive observations of the fundus of an eye (eyeground).

Diseases of the eye fundus (e.g. the age-related macular degeneration) are frequently accompanied with microscopic physiological changes, which cannot be diagnosed extrinsically (non-invasively) with conventional methods. Thus for example, age-related macular degeneration is accompanied with the deposit of fluorescent pigments in the retinal pigment epithelium (RPE).

Investigations on histological preparations by means of electron beam microscopy and high resolution light optical methods with a short working distance have revealed that granula are formed as an intracellular correlate of these pigments, the granula having a size of approximately 1 μm.

Due to the distance between the fundus and the eye-lens, the spatial resolution of conventional non-invasive imaging methods is not sufficient to analyse these fine fluorescent structures directly at the patient. Furthermore, there are many disturbing effects due to auto-fluorescence, diffraction and scattering outside the object plane.

Conventional wide-field fundus cameras suffer from a low contrast. Thus, so-called scanning laser ophthalmoscopes (SLOs), which belong to confocal microscopes, have been proposed to investigate the fundus with high resolution. A scanning laser ophthalmoscope scans the fundus point-by-point by a focused laser beam resulting in an improved contrast compared to a conventional fluorescent fundus camera.

In order to further increase the resolution of scanning laser ophthalmoscopes, adaptive optics may be used to compensate for the disturbing effects of lens aberrations. By means of adaptive optics, the resolution of the scanning laser ophthalmoscopes may be increased from 5-10 μm to 2-3 μm. However, the use of adaptive optics is complex and cost-intensive.

Other approaches to increase the resolution and particularly the contrast of images of the fundus use two-photon excitation. The concept of the two-photon microscopy is based on a fluorescence excitation which requires the energy of two photons, i.e., fluorescence excitation only occurs when two photons are absorbed. In such a system, the intensity of fluorescent light emitted by the specimen depends quadratically on the intensity of the excitation light. Therefore, much more two-photon fluorescence is generated where the illumination beam is tightly focused than where it is more diffuse. Accordingly, excitation is restricted to a small focal volume, resulting in an effective rejection of out-of-focus objects. The observed specimen is scanned by the focused excitation light. Usually, also the detection is realized in focus resulting in a confocal microscopy method with a two-photon excitation. Since the probability of the near-simultaneous absorption of two photons is extremely low, high energy densities of the excitation light (laser power and focusing) are required. Therefore, due to temporary high local thermal exposures an application in connection with humans, particularly in ophthalmoscopy, is problematic. Since the fundamental requirements for light hazard protection (ISO 15004-2:2007) have to be met, only relatively small energy densities are allowed in connection with ophthalmic instruments, which may lead to a low signal-to-noise relation. An expensive laser system and a relatively complex arrangement are further drawbacks of the two-photon technique.

Moreover, another difficulty frequently occurring in the field of ophthalmology is that a healthy eye, which is not fixed, permanently carries out eye movements, even when the eye is kept subjectively still. Such movements are usually considered to be obstructive for imaging the fundus. Particularly the quasi-stochastic micro-saccades, i.e. jerky or abrupt movements of the eye typically in the range of 3 to 50 angular minutes, may imply significant lateral shifts of an observed region when observing this region with a high resolution.

BRIEF DESCRIPTION

The embodiments described herein provide an improved method, apparatus, computer implemented method and a computer program product for noninvasive observations of the eye fundus.

According to one aspect, there is provided a method for non-invasive observations of a fundus, the method including illuminating a retinal region of an eye by projecting an illumination pattern of illumination light onto the retinal region of the eye, detecting at least a portion of fluorescent light emitted from the retinal region of the eye and/or detecting at least a portion of illumination light reflected from the retinal region of the eye, thereby capturing a series of images of the retinal region of the eye at a plurality of different relative positions of the retinal region of the eye with respect to the illumination pattern projected onto the retinal region of the eye, wherein between the capturing of at least two images of the series the relative position of the retinal region of the eye with respect to the illumination pattern projected onto the retinal region of the eye is shifted in a non-controlled manner, processing the captured images to extract a sub-resolution image of the retinal region of the eye.

According to another aspect, there is provided an ophthalmoscope for non-invasive observations of a fundus, the ophthalmoscope including a light source which emits illumination light, a pattern generation system arranged in the optical path of the illumination light, the pattern generation system configured to generate an illumination pattern of the illumination light, at least one objective arranged and configured to illuminate the retinal region of an eye by projecting the illumination pattern onto the retinal region of the eye, an image capturing system configured to detect at least a portion of fluorescent light emitted from the retinal region of the eye and/or detect at least a portion of illumination light reflected from the retinal region of the eye, thereby capturing a series of images of the retinal region of the eye at a plurality of different relative positions of the retinal region of the eye with respect to the illumination pattern projected onto the retinal region of the eye, wherein between the capturing of at least two images of the series the relative position of the retinal region of the eye with respect to the illumination pattern projected onto the retinal region of the eye is varied or shifted in a non-controlled manner, and a data processing system configured to process data obtained from the plurality of captured images, thereby producing a sub-resolution image of the retinal region of the eye.

According to yet another aspect, there is provided a computer implemented method for generating sub-resolution images of a fundus based on a plurality of raw images of the retinal region of the eye obtained by an ophthalmoscope, wherein said plurality of raw images is obtained by projecting an illumination pattern of illumination light onto the retinal region of the eye, thereby illuminating the retinal region of the eye, detecting at least a portion of fluorescent light emitted from the retinal region of the eye and/or detecting at least a portion of illumination light reflected from the retinal region of the eye, thereby capturing a series of images at a plurality of different relative positions of the retinal region of the eye with respect to the illumination pattern projected onto the retinal region of the eye, wherein between the capturing of at least two images of the series the relative position of the retinal region of the eye with respect to the illumination pattern projected onto the retinal region of the eye is varied or shifted in a non-controlled manner; said method comprising the steps of receiving said plurality of images of the retinal region of the eye, for each received image determining the non-controlled shift of the relative position of the retinal region of the eye with respect to the illumination pattern projected onto the retinal region of the eye, a-posteriori shifting of each received image to reverse the corresponding stochastic variation or shift of the retinal region of the eye with respect to the projected illumination pattern, thereby obtaining a corresponding shifted image (i.e. a corresponding a-posteriori shifted image), and processing the shifted images (i.e. the a-posteriori shifted images) to extract a sub-resolution image.

The method for non-invasive observations of a fundus, the ophthalmoscope for noninvasive observations of a fundus, the computer implemented method for generating sub-resolution images of a fundus and the computer program product described herein offer one or more of the following advantages: For a numerical aperture (NA) which may be in the range of 0.1 to 0.5 in order to obtain working distances of several centimeters advantageous for ophthalmoscope observations, the optical resolution of the ophthalmoscope described herein can be improved by a factor of 2 or more compared to conventional systems having the same numerical aperture. Despite the low numerical apertures and large working distances, a resolution in the range of few micrometers and a contrast comparable to the best available scanning laser ophthalmoscopes (SLO) can be achieved. Thus, by the methods and the apparatus (ophthalmoscope) according to the disclosure, the retinal pigment epithelium (RPE) can be observed or imaged with a resolution allowing the recognition of single cells of the RPE. This is not possible with at least some known systems.

Furthermore, according to an aspect, quasi-stochastic movements of the eye (particularly micro-saccades of the eye), which are usually considered to be obstructive for imaging the fundus, can be exploited to improve the resolution and the contrast of the obtained images. This results in a less complex, cost-effective method and apparatus (ophthalmoscope) for non-invasive fluorescence observations of the fundus. Further, the error-proneness can be reduced.

The combination of high optical resolution and large working distances is of high general importance not only for ophthalmoscopic application, but also for many other biological and medical applications or any other (non-biological) applications requiring a large working distance. The proposed ophthalmoscope, the corresponding methods and the computer program product offer the possibility of an in vivo imaging.

Moreover, according to an aspect, the eye is subjected to a wide-field illumination. Thus, it is not necessary to subject the eye to light with high illumination intensity and/or energy densities which might degrade or damage it. Further, disturbing influences of auto-fluorescence, scattering and diffraction in regions outside the focus plane can be reduced.

Another advantage of the ophthalmoscope described herein may be that low-cost pattern generation devices (for example micro liquid crystal displays) can be used for structuring/patterning the illumination light illuminating the eye. Accordingly, an ophthalmoscope with a less costly, less critical and more stable optical setup as compared to prior art solutions may be realized.

A further advantage may be the reduction in the requirements for the stability of the optical set up of the ophthalmoscope and in particular the requirements for stability of the illumination during the acquisition of the series of images of the observed retinal region of the eye. This simplifies the optical set up of the ophthalmoscope, while improving its resolution.

The use of the structured or patterned illumination may reduce the influence of disturbing effects due to auto-fluorescence, diffraction and scattering outside the object plane, thereby obtaining a significant improvement of resolution and contrast.

In addition, the method for non-invasive fluorescence observations of an eyeground and the corresponding ophthalmoscope according to an aspect may be efficiently combined with other microscopic techniques, for example with localization microscopy and/or fluorescence tomography and/or other 3D techniques. Such a combined application is particularly suitable in cases where an eye tissue has to be removed for medical reasons, or in cases of experimental studies using animal models.

Further, it is possible to apply wavefront compensation by means of adaptive optics. Thereby, an additional improvement of the imaging may be achieved particularly in the cases that lens aberrations or inhomogeneous refractive indices in the specimen are present, as it is the case when the observed specimen is an eye.

The above and other features and advantages will become more apparent upon reading of the following detailed description of exemplary embodiments and accompanying drawings. Other features and advantages of the subject-matter described herein will be apparent from the description and the drawings and from the claims. It should be understood that even though embodiments are separately described, single features and functionalities thereof may be combined without prejudice to additional embodiments.

BRIEF DESCRIPTION OF THE DRAWINGS

Exemplary embodiments of are exemplarily described regarding the following figures.

FIGS. 3A and 3B show two exemplary images of a portion of an eye retina, wherein FIG. 3A shows an image obtained by a conventional microscope and FIG. 3B shows an image obtained by a structured illumination microscope (SMI).

FIGS. 6A-6F are schematic illustrations of the determination of the non-controlled (e.g. stochastic/random) shift of the relative position of the specimen (e.g. an eye) with respect to the illumination pattern projected onto the specimen.

Throughout the figures, same reference signs are used for the same or similar elements.

DETAILED DESCRIPTION

Figure 1A:
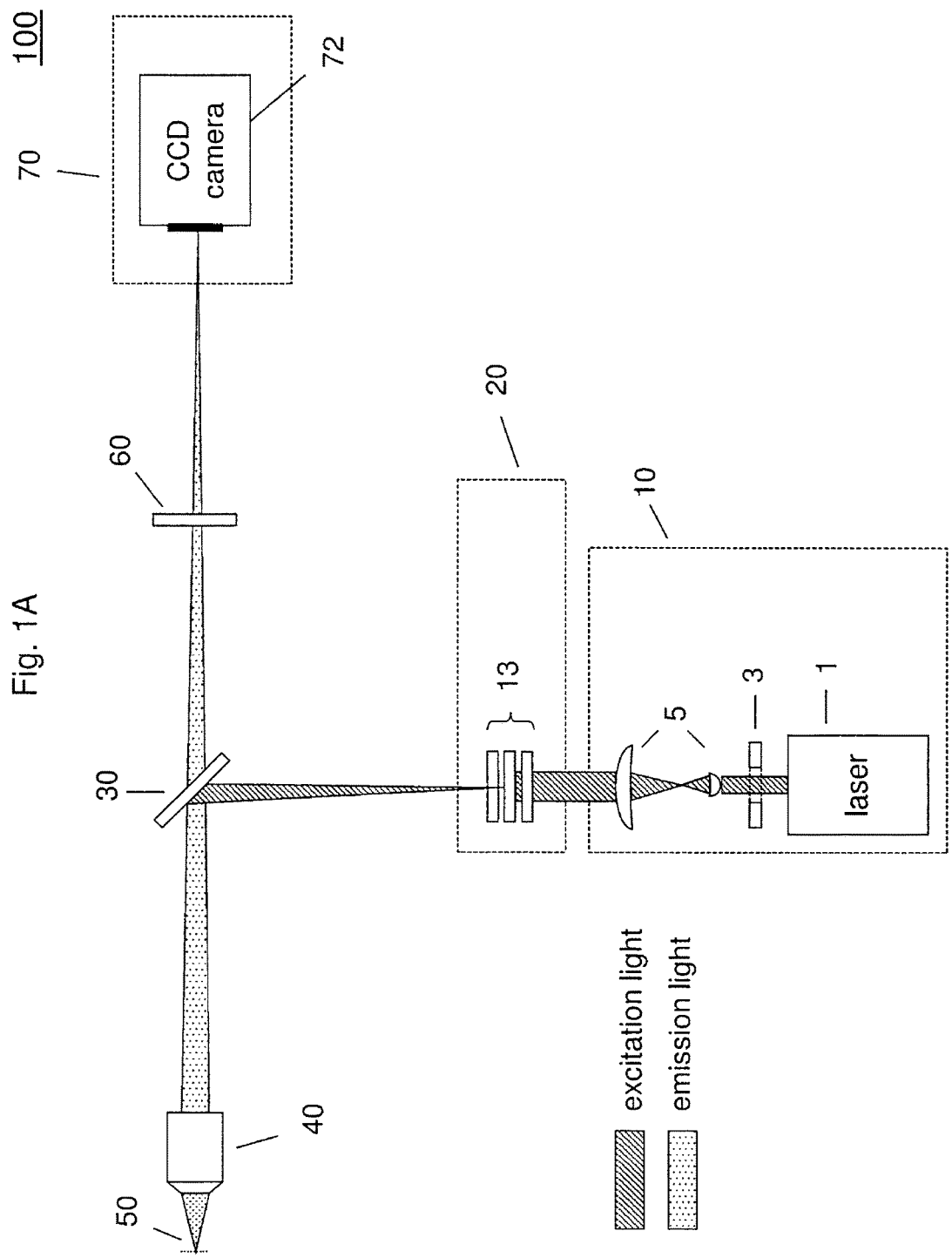
FIG. 1A shows a schematic representation of an optical arrangement of an ophthalmoscope according to one example.

According to an example, there is provided a method for non-invasive observations of a fundus. The method includes illuminating a retinal region of an eye by projecting an illumination pattern of illumination light onto the retinal region of the eye and detecting at least a portion of fluorescent light emitted from the retinal region of the eye and/or detecting at least a portion of illumination light reflected from the retinal region of the eye, thereby capturing a series of raw images of the retinal region of the eye at a plurality of different relative positions of the retinal region of the eye with respect to the illumination pattern projected onto the retinal region of the eye. Between the capturing of at least two images of the series (for example between the capturing of each two consecutive images of the series) the relative position of the retinal region of the eye with respect to the illumination pattern projected onto the retinal region of the eye is shifted in a non-controlled manner. The method includes further processing the captured raw images to extract a sub-resolution image of the retinal region of the eye.

The term "fundus" is used herein as "fundus oculi", "fundus of the eye" or "eyeground".

The term "retinal region of an eye" in the sense of the present application also comprises cellular layers like the retinal pigment epithelium (RPE), which are located below the retina. In other words, the term "retinal" may be understood herein as "retinal/subretinal".

The term "sub-resolution" (also called "super-resolution") within the scope of this disclosure encompasses a resolution which is better than the conventional diffraction limited resolution, i.e. better than the resolution given by the Abbe limit. A microscope, particularly an ophthalmoscope, having "sub-resolution" may thus be able to distinguish structures that are not expected to be distinguishable according to the Abbe limit. In other words, a sub resolution image is an image with an enhanced optical resolution compared with a scanning laser ophthalmoscope (SLD) according to the state of the art applied at the same illumination wavelength and with the same numerical aperture of the objective lens used for imaging.

The term "fluorescence" or "fluorescent" within the scope of this disclosure encompasses any photon interactions, in which differences arise between the excitation spectrum and the emission spectrum of the same substance, which are not attributable to monochromatic absorption or dispersion. The term "fluorescence" may include in particular multiphoton interactions, in which the excitation wavelength can be greater than the emission wavelength. The term "fluorescence" encompasses thus the closely related phenomena of fluorescence, phosphorescence and luminescence, which differ in particular in the fluorescence lifetime.

The expression "a series of images" within the scope of this disclosure encompasses a plurality of images.

In the following the images captured by illuminating the retinal region of the eye by an illumination pattern and detecting at least a portion of the fluorescent light emitted from the illuminated retinal region of the eye and/or detecting at least a portion of illumination light reflected from the retinal region of the eye will be also referred to as "raw" images, in order to better distinguish them from the "sub-resolution" images obtained by processing the captured "raw" images. This does not exclude the possibility of subjecting the images detected by the detector to suitable image pre-processing operations, such as noise filtering, in order to improve their image quality. The term "raw images" also encompasses such pre-processed images.

The non-invasive observations may comprise non-invasive fluorescence observations and/or non-invasive reflection observations.

In case of non-invasive fluorescence observations, the illumination light encompasses excitation light to excite fluorescent material (e.g. fluorochromes). The eye, particularly the fundus, may contain a plurality of fluorochromes, i.e. chemical compounds that can re-emit light upon light excitation. For example, in the eye (fundus) autofluorescent lipofuscin is located in the retinal pigment epithelium. The fluorescence light emitted from this fluorochrome may be detected, thereby forming an image of the observed retinal region. It is also possible to use (e.g. artificial) fluorescent markers or labels (e.g. fluorescein) to label specific regions or structures (e.g. blood vessels) in the back of the eye and image them, or to apply any other suitable labeling scheme.

In case of non-invasive reflection observations, the illumination light may be reflected at the fundus of the eye or at one or more parts of the fundus of the eye. At least a portion of the reflected light may be detected, thereby forming an image of the observed retinal region of the eye.

The retinal region of an eye is illuminated by projecting an illumination pattern of illumination light (e.g. excitation light) onto it. More specifically, the illumination pattern of illumination light is projected into an object plane where the retinal region of the eye is located. The object plane may be a plane perpendicular to the optical axis of the ophthalmoscope and more specifically to the optical axis of at least one ophthalmoscope objective. The illumination pattern of illumination light may include illumination light which is periodically or non-periodically spatially modulated in its intensity and/or phase. The illumination pattern of illumination light may be a suitably spatially structured or patterned illumination light, in particular an illumination light, which is suitably spatially modulated in the object plane. An example of such spatially modulated illumination pattern is a fringe pattern or a combination of more than one fringe patterns.

In an embodiment the ophthalmoscope for carrying out the observations of the retinal region of the eye comprises one objective through which the specimen/object is illuminated and/or reflected light or fluorescent light is detected. It is also possible to employ arrangements with two or more objectives, through which the specimen/object is detected and reflected light or fluorescent light is detected.

The illumination pattern of illumination light may be generated by various means, for example by a diffraction grating, a spatial light modulator, an interferometer or other suitable means. In an example, the illumination pattern may be generated by conducting an illumination light emitted from a light source through an intensity modulating light transmitting spatial light modulator arranged in the optical path of the illumination light (i.e. in the illumination arm or path of the ophthalmoscope). The intensity modulating light transmitting spatial light modulator may be constituted by or may include a micro liquid crystal display (micro-LCD), such as for example used in mass produced light projectors. The micro-LCD may display a pattern structure in an image plane perpendicular to the beam path (i.e. perpendicular to the direction of propagation of the illumination light). Thus, illumination light transmitted through the micro-LCD is spatially modulated by the displayed pattern or structure in the image plane. The modulated, i.e. structured or patterned illumination light may then be focused into the object plane. In other words, the pattern or structure displayed in the image plane may be projected onto the retinal region of the eye located in the object plane. In another example, fixed diffraction grating or a plurality of diffraction grating may be used for patterning the illumination light.

Upon illuminating the retinal region of the eye, fluorescent light may be emitted and/or illumination light may be reflected from the retinal region of the eye or from one or more parts of the retinal region of the eye, wherein at least a portion of said fluorescent light and/or reflected light is detected. The detection of the fluorescent light and/or reflected light may be carried out by means of an imaging system, also referred to as an image capturing system, which may include a CCD camera. By detecting the fluorescent light and/or reflected light of the eye (and optionally pre-processing the detected images, for example to improve the image quality), a raw image of the retinal region of the eye is acquired or captured by the imaging system. This procedure may be repeated so that a plurality or a series of raw images is captured.

The relative position of the retinal region of the eye with respect to the illumination pattern projected onto the retinal region of the eye is varied or shifted in a non-controlled manner (i.e. in a manner that is not perfectly controllable or in other words not perfectly deterministic). The expression "in a non-controlled manner" within the scope of the disclosure encompasses also the expressions "in an undetermined manner", "non-deterministically" or "involuntarily". An example of a non-controlled shift or variation may be a "quasi linear" shift or variation. Another example is a quasi-stochastic or stochastic (i.e. pseudo-random or random) shift or variation, for example a quasi-stochastic or stochastic shift or variation in a two dimensional space.

A shift in a non-controlled manner may be realized for example by using the intrinsic saccadic movement of the eye and/or by using intrinsic movements and/or involuntary movements of the patient whose eye is observed (e.g. intrinsic, non-controlled movements of the patient's head). A shift in a non-controlled manner may also be realized by using the (intrinsic) instability and impreciseness of one or more optical components of the used illumination and/or image capturing system, i.e. of the used optical setup.

Alternatively or in addition, a non-deterministic, stochastic or random shift may be obtained by actively varying the relative position of the illumination pattern with respect to the observed region. Due to the non-controlled (e.g. stochastic) shift, the relative position of the retinal region of the eye with respect to the illumination pattern projected onto it changes between two captured images. Accordingly, a plurality of raw images is captured at a plurality of different relative positions of the retinal region of the eye with respect to the illumination pattern projected onto the retinal region of the eye. In particular, three or more (for example up to 100) raw images may be captured at three or more different relative positions of the retinal region of the eye with respect to the illumination pattern projected onto the retinal region of the eye.

In an example, the uncontrolled variation of the observed eye's position with respect to the optical set-up and more specifically with respect to the optical plane of the illumination pattern, the image plane or at least one objective lens may be used to realize the non-controlled shift of the relative position of the retinal region of the eye with respect to the illumination pattern between the capturing of the at least two (for example consecutive) images and thus the plurality of different relative positions of the retinal region of the eye with respect to the illumination pattern at which images are captured.

Advantageously, the inherent stochastic or quasi-stochastic movement of the eye itself, such as the saccadic eye movement, may be used in the method for non-invasive fluorescence observations of a fundus using an ophthalmoscope. In case of letting the eye shift, i.e. in case of using saccadic eye movements, the illumination pattern, i.e. the illumination pattern of illumination light (e.g. excitation light), may be left unchanged. Alternatively or in addition, involuntary head or body movement of the patient may be used.

Still further alternatively or in addition, the stochastic shift or variation may be achieved by non-controllable, non-deterministic movements of the optical set-up, such as a stochastic stage scanning, i.e. a stochastic movement of the illumination pattern. For example, if the illumination pattern is produced by a spatial light modulator (such as a micro-LCD), the illumination pattern may be shifted or varied by means of the DVI port of a computer that drives a controller of the spatial light modulator. Alternatively or in addition, the stochastic shift of the relative position of the retinal region of the eye with respect to the illumination pattern may be achieved by a stochastic movement of a focusing lens system of at least one ophthalmoscope objective.

Accordingly, in an example the relative position of the retinal region of the eye with respect to the illumination pattern projected onto it may be stochastically shifted or varied by utilizing stochastic saccades of the eye (i.e. the saccadic eye movements) and/or stochastic stage scanning and/or stochastic movement of a focusing lens system of at least one ophthalmoscope objective.

In order to extract a sub-resolution image of the retinal region of the eye, the captured raw images are further processed. The processing of the captured raw images may comprise a-posteriori shifting of each captured raw image to reverse the corresponding stochastic shift (variation) of the relative position of the retinal region of the eye with respect to the projected illumination pattern, thereby obtaining shifted images; and processing the shifted (raw) images to extract a sub-resolution image of the retinal region of the eye.

The a-posteriori shifting of each captured raw image to reverse the corresponding non-controlled (e.g. stochastic) shift of the retinal region of the eye with respect to the projected illumination pattern may comprise frequency filtering the captured raw images to remove the primary illumination pattern information from the images; and iteratively shifting the filtered images.

The amount of the a-posteriori shift of each captured raw image (i.e. the second and each subsequent raw image out of the series of captured raw images) to reverse the non-controlled (stochastic/random) shift of the specimen (e.g. the retinal region of an eye) with respect to the projected illumination pattern may be determined in the following manner:

The periodic illumination pattern $I_{Illu}$ can be written as a sum of sinusoidal functions with different spatial periods $\Delta k_i$ and phases $\phi_i$.

$$I_{Illu}(x) = \Sigma_i \cos(x \Delta k_i - \phi_i) \tag{1}$$

A primary image (reference image), which may be the first captured image out of a series of captured images at different relative positions of the retinal region of the eye with respect to the projected illumination pattern, is given by $$Im_0(x) = (\rho_0(x) \cdot I_{Illu}(x)) * PSF(x) \tag{2}$$

where $\rho$ is the fluorophore distribution, PSF the point spread function, and where * denotes the convolution operator.

In another image $Im_1$ (for example a second or a subsequent image of the series of captured images), the specimen is shifted by a vector $\Delta x$ with respect to the primary (reference) image. The shift can be expressed by a convolution with the delta distribution:

$$\rho_1(x) = \rho_0(x - \Delta x) = \rho_0(x) * \delta(x - \Delta x) \tag{3}$$

This gives the second or a subsequent image of the series $$Im_1(x) = ([\rho_0(x) * \delta(x - \Delta x)] \cdot I_{Illu}(x)) * PSF(x) \tag{4}$$

A Fourier transform (FT, symbolized by a tilde over the corresponding function) of the above expressions (2) and (4) gives $$\widetilde{Im}_0(k) = (\widetilde{\rho_0}(k) * \widetilde{I_{Illu}}(k)) \cdot OTF(k) \tag{5}$$

and $$\widetilde{Im}_1(k) = \left(\left[\widetilde{\rho_0}(k) \cdot \frac{1}{(2\pi)^2}\exp(-ik\Delta x)\right] * \widetilde{I_{Illu}}(k)\right) \cdot OTF(k) \tag{6}$$

where the optical transfer function OTF is the Fourier transform of the point spread function PSF and the Fourier transform of the illumination pattern $\widetilde{I_{Illu}}(k)$ is given by $$\widetilde{I_{Illu}}(k) = \Sigma_i \exp(i\phi_i)\delta(k - \Delta k_i) + \exp(-i\phi_i)\delta(k + \Delta k_i) \tag{7}$$

Therefore, the Fourier transformed primary image $\widetilde{Im}_0(k)$ and the Fourier transformed second or subsequent image $\widetilde{Im}_1(k)$ become $$\widetilde{Im}_0(k) = [\Sigma_i \exp(i\phi_i)\widetilde{\rho_0}(k - \Delta k_i) + \exp(-i\phi_i)\widetilde{\rho_0}(k + \Delta k_i)] \cdot OTF(k) \tag{8}$$

$$\widetilde{Im}_1(k) = \left[\sum_i \exp(i\phi_i)\widetilde{\rho_0}(k - \Delta k_i) \cdot \frac{1}{(2\pi)^2}\exp(-i(k - \Delta k_i)\Delta x) + \exp(-i\phi_i)\widetilde{\rho_0}(k + \Delta k_i) \cdot \frac{1}{(2\pi)^2}\exp(-i(k + \Delta k_i)\Delta x)\right] \cdot OTF(k) \tag{9}$$

The expression for the Fourier-transformed image $\widetilde{Im}_1(k)$ (e.g. the second or subsequent image) can be reorganized in the following manner:

$$\widetilde{Im}_1(k) = \left[\frac{1}{(2\pi)^2}\exp(-ik\Delta x)\sum_i \exp(i\phi_i)\widetilde{\rho_0}(k - \Delta k_i) \cdot \exp(i\Delta k_i \Delta x) + \exp(-i\phi_i)\widetilde{\rho_0}(k + \Delta k_i) \cdot \exp(-i\Delta k_i \Delta x)\right] \cdot OTF(k) \tag{10}$$

with the identities $$\exp(i\Delta k_i \Delta x) = \cos(i\Delta k_i \Delta x) + i \sin(i\Delta k_i \Delta x) \tag{11}$$

$$\exp(-i\Delta k_i \Delta x) = \cos(i\Delta k_i \Delta x) - i \sin(i\Delta k_i \Delta x) \tag{12}$$

The Fourier transform of the image $\widetilde{Im}_1(k)$ (e.g. the second or subsequent image) then becomes:

$$\widetilde{Im}_0(k) = \left[\frac{1}{(2\pi)^2}\exp(-ik\Delta x)\sum_i \cos(i\Delta k_i \Delta x) \right.$$
$$(\exp(i\phi_i)\widetilde{\rho_0}(k - \Delta k_i) + \exp(-i\phi_i)\widetilde{\rho_0}(k + \Delta k_i)) +$$
$$\left. i \sin(i\Delta k_i \Delta x)(\exp(i\phi_i)\widetilde{\rho_0}(k - \Delta k_i) - \exp(-i\phi_i)\widetilde{\rho_0}(k + \Delta k_i))\right] \cdot$$
$$OTF(k). \tag{13}$$

Apparently, the first term of the sum becomes $$\widetilde{Im}_0(k) \cdot \Sigma_i \cos(i\Delta k_i \Delta x) \tag{14}$$

The non-controlled (for example stochastic/random) shift vector $\Delta x$ can be obtained by applying an analytic deconvolution of $Im_1(x)$ by $Im_0(x)$ in the form of $$R(x) = iFT\left(\frac{FT(Im_1(x))}{FT(Im_0(x))}\right) = iFT\left(\frac{\widetilde{Im}_1(k)}{\widetilde{Im}_0(k)}\right). \tag{15}$$

wherein iFT denotes the inverse Fourier transform.

The division of the Fourier-transformed second or subsequent image by the primary image $$\frac{\widetilde{Im}_1(k)}{\widetilde{Im}_0(k)}$$

may be carried out pixel by pixel. Hence, the analytic deconvolution $R(x)$ becomes $$R(x) = iFT\left[\frac{\frac{1}{(2\pi)^2}\exp(-ik\Delta x)\sum_i \cos(i\Delta k_i \Delta x) + \sum_i i \sin(i\Delta k_i \Delta x)(\exp(i\phi_i)\widetilde{\rho_0}(k - \Delta k_i) - \exp(-i\phi_i)\widetilde{\rho_0}(k + \Delta k_i))}{\Sigma_i \exp(i\phi_i)\widetilde{\rho_0}(k - \Delta k_i) + \exp(-i\phi_i)\widetilde{\rho_0}(k + \Delta k_i)}\right] \cdot OTF(k). \tag{16}$$

The second term depends on $\rho_0(x)$. It is called $\widetilde{pert1}(k)$ in the following.

When performing the inverse Fourier transformation iFT, R(x) becomes $$R(x) = \delta(x - \Delta x) \cdot \sum_i \cos(i\Delta k_i \Delta x) + \quad (17)$$

$$\delta(x - \Delta x) * iFT \left[ \frac{\sum_i i\, \sin(i\Delta k_i \Delta x)(\exp(i\varphi_i)\widetilde{\rho_0}(k - \Delta k_i) - \exp(-i\varphi_i)\widetilde{\rho_0}(k + \Delta k_i))}{\sum_i \exp(i\varphi_i)\widetilde{\rho_0}(k - \Delta k_i) + \exp(-i\varphi_i)\widetilde{\rho_0}(k + \Delta k_i)} \right],$$

wherein the second part is called pert2 (x). This gives $$R(x) = \delta(x-\Delta x)\cdot\Sigma_i \cos(i\Delta k_i \Delta x) + \text{pert2}(x) \quad (18).$$

The sum in this expression is constant. In practice, the position of the peak of the delta function in (x), and thus the shift vector $\Delta x$, can be found easily despite of the perturbation pert2(x). In particular, the shift vector $\Delta x$ describing the shift of the relative position of the specimen (e.g. an eye or the retinal region thereof) with respect to the projected illumination pattern, which occurred between the capturing of the primary image and the capturing of the second or subsequent image, can be obtained by determining the position of the maximum in intensity (i.e. the peak) of the analytic deconvolution R(x). This approach is schematically illustrated in FIGS. 6A-6F which are described in more detail below.

In summary, the processing of the captured images may comprise determining the non-controlled shift of the relative position of the retinal region of the eye with respect to the illumination pattern projected onto the retinal region of the eye for each image of the series. More specifically, the non-controlled (e.g. stochastic/random) shift which occurred between the capturing of a particular image of the series and the capturing of a reference image may be determined. Subsequently, each image of the series may be subjected to an a-posteriori shifting to reverse the determined shift of the relative position of the retinal region of the eye with respect to the projected illumination pattern, thereby obtaining a corresponding shifted image. The shifted images may be processed to extract a sub-resolution image of the retinal region of the eye.

The reference (primary or unshifted) image may be for example a first image in the series of images of the observed retinal region of the eye. Each subsequent image of the series may be shifted in an uncontrolled manner (e.g. by random/stochastic shifting) with respect to the primary image.

The non-controlled shifts of the relative position of the retinal region of the eye with respect to the illumination pattern projected onto the retinal region of the eye for each image of the series may be determined by applying an analytic deconvolution of each of the images of the series by a primary, unshifted image (reference image) to obtain a corresponding deconvolved image and determining the position of a maximum of the analytic deconvolution of each of the deconvolved images. For each of the images of the series, the non-controlled shift of the relative position of the retinal region of the eye with respect to the illumination pattern projected onto the retinal region of the eye may be determined from the respective position of the maximum of the analytic deconvolution.

The determining of the non-controlled shift of the specimen (e.g. the retinal region of the eye) between a captured first image $Im_0$ (reference image) and a captured second image $Im_1$ may include Fourier-transforming the captured first image and the captured second image, dividing the Fourier-transformed second image by the Fourier-transformed first image to obtain a divided image, wherein the dividing may be performed pixel by pixel, i.e. each pixel of the first image is divided by a corresponding pixel of the second image, inverse Fourier-transforming the divided image, and determining the position of a maximum of intensity of the inverse Fourier-transformed divided image (i.e. the intensity peak P of the divided image, which results from the delta function, see equation 18).

The position of a maximum of intensity of the inverse Fourier-transformed divided image represents the non-controlled shift of the relative position of the retinal region of the eye with respect to the illumination pattern projected onto the retinal region of the eye, which occurred between the capturing of the first image and the capturing of the second image (i.e. the non-controlled shift which is associated with the second image).

The second image $Im_1$ may then be shifted a-posteriori by the obtained shift to reverse the corresponding non-controlled (e.g. stochastic/random) shift of the specimen (retinal region of the eye) with respect to the projected illumination pattern and to produce a shifted image. This can be accomplished, for example, by first frequency filtering the images to remove the primary illumination pattern information from the images and afterwards shifting the images iteratively. The a-posteriori shifting of the second image may also be accomplished by multiplying the Fourier transform of the image with $\exp(ik\Delta x)$ and transforming it back to the real space. Other methods may also be used.

The same procedure may be repeated for all images (i.e. the third and each subsequent image out of the series of captured raw images) which are associated with a plurality of different shifts (i.e. relative positions of the specimen with respect to the projected illumination pattern). That is, also the third and each subsequent image of the series is Fourier-transformed and the Fourier-transformed third and each subsequent image of the series is divided by the Fourier-transformed first image to obtain corresponding divided images. Each divided image may then be Fourier-transformed and the corresponding positions of a maximum of intensity of the inverse Fourier-transformed divided images, and thus, the corresponding non-controlled shifts (which respectively occurred between the capturing of the first image and the capturing of the third and each subsequent image of the series), may be determined in an analog manner as described above.

The subsequent processing of the shifted images to extract a sub-resolution image may comprise applying conventional frequency space based SMI reconstruction algorithms as described, e.g. in R. Heintzmann and C. Cremer, "Laterally modulated excitation microscopy: Improvement of resolution by using a diffraction grating", proceedings of SPIE (1999), 3568, 185. Since these methods are known, a detailed description thereof will be omitted.

The illumination pattern may be projected onto the retinal region of the eye through at least one objective (in particular one, two or three objectives) of the ophthalmoscope having a numerical aperture of less than 0.5. The numerical aperture of the at least one objective may be equal or larger than the numerical aperture of the eye which is approximately 0.1. Accordingly, the numerical aperture of the at least one objective may be in the range of 0.1 to 0.5 or in the range of 0.2 to 0.5. The use of a low numerical aperture objective enables large working distances, for example working distances in the range of several centimeters (in particular larger than 5 cm, more particularly larger than 10 cm and even more particularly larger than 15 cm). Due to the relatively large working distances and at the same time high resolution, the method for non-invasive fluorescence and/or reflection observations of an eyeground using an ophthalmoscope having such large working distances is suitable for in-vivo imaging.

The illumination of the retinal region of the eye may be synchronized with the detecting at least a portion of fluorescent or reflected light and/or with the capturing of the raw images, so that the retinal region of the eye may be illuminated only when images are captured. For example, the illumination light may be a stroboscopic light, i.e. may be switched on- and off, for example in a millisecond frame. In particular, the illumination light (for example excitation light) may be only projected onto the retinal region of the eye (said on-time) when the camera acquires an image and may be switched off or redirected away from the retinal region of the eye (said off-time) when the camera reads out. This reduces probability of eye damages due to permanent illumination during eye observation.

The duration of the on-times during which the retinal region of the eye is illuminated may be shorter than the duration of the off-times during which the illumination of the retinal region of the eye is interrupted. For example, the probability of saccadic eye movement during the illumination timeframe may be generally low, whereas the probability for a movement during the off-times is higher. Thus, the distance the retinal region of the eye moves during the on-time may be shorter than the distance the retinal region of the eye moves during the off-time. For example, the on-time (illumination and acquisition) timeframes may be of order of 10 ms and the off-times/timeframes may be of order of 100 ms. Accordingly, the captured images are less blurred and the overall illumination time can be significantly reduced. Further, the eye is not subjected to a permanent illumination which might degrade or damage it.

Figure 4:
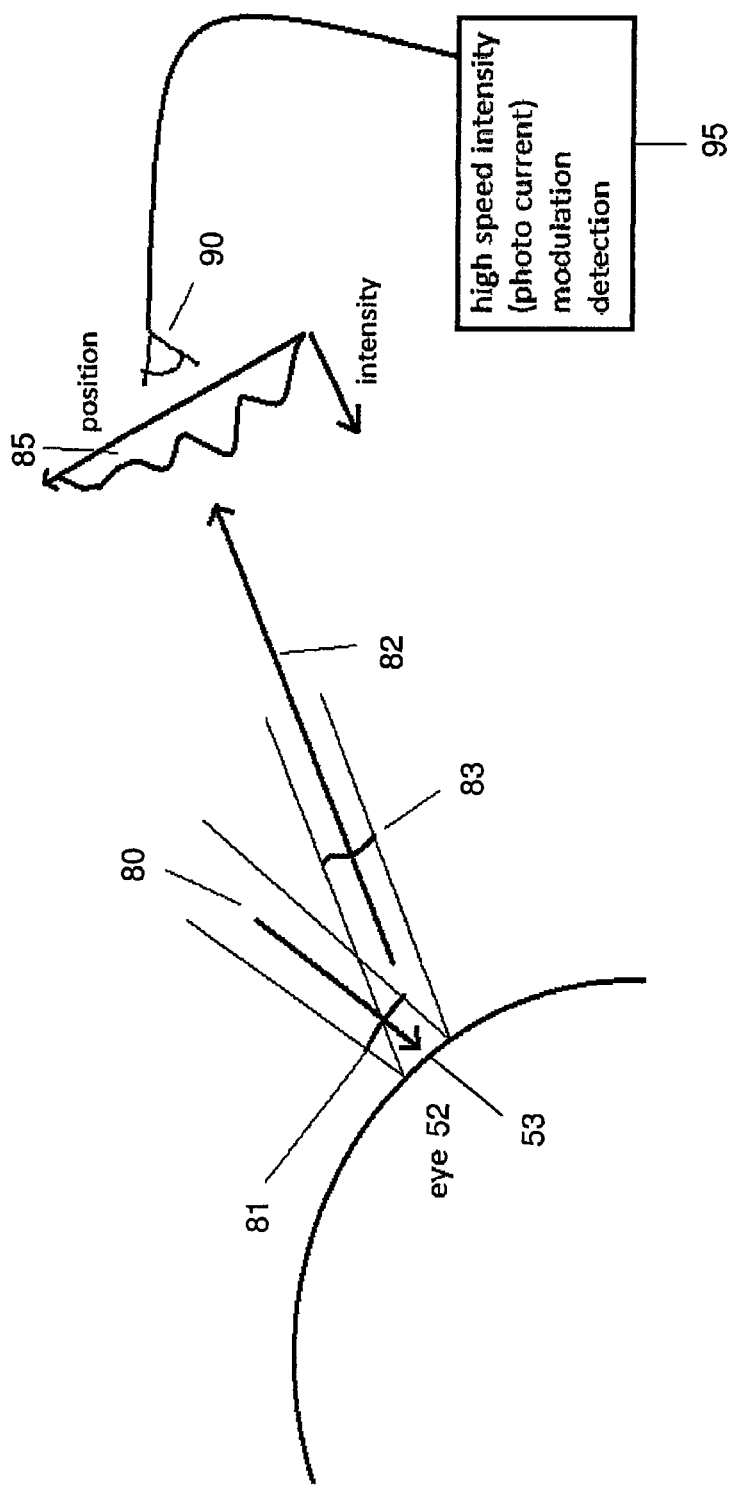
FIG. 4 is a schematic view of a saccade detection device which works with reflected light.

The illumination and image acquisition may advantageously be triggered shortly after a stochastic shift of the relative position of the retinal region of the eye with respect to the illumination pattern projected onto the retinal region of the eye, particularly after a saccadic movement of the eye. The trigger signal could be given by a high speed saccade detection device using state of the art methods or a modified detection method as indicated in FIG. 4. By the application of such an additional device, the number of redundant and faulty raw images can be reduced.

Accordingly, the method may further include the steps of detecting stochastic variation or shifts of the relative position of the retinal region of the eye with respect to the illumination pattern projected onto the retinal region of the eye, and synchronizing the illumination of the retinal region of the eye and/or the capturing a series of raw images with the detected stochastic variation or shifts of the relative position of the retinal region of the eye with respect to the illumination pattern projected onto the retinal region of the eye.

By synchronizing the illumination of the retinal region of the eye with the detected stochastic shifts of the relative position of the retinal region of the eye with respect to the illumination pattern projected onto the retinal region of the eye, the overall illumination time of the eye can be reduced and damage of the eye can be prevented.

The method may further include a step of sorting-out one or more of the captured raw images, wherein a particular raw image is sorted out if it is determined that the stochastic variation or shift of the relative position of the retinal region of the eye with respect to the illumination pattern projected onto the retinal region of the eye during the capturing of the raw image exceeds a predetermined threshold.

If the stochastic variation or shift of the relative position of the retinal region of the eye with respect to the illumination pattern projected onto it during a certain on-time exceeds a predetermined threshold, derived from the suitability of this threshold for the reconstruction of a sub-resolution image, the according raw image will be blurred. The predetermined threshold may be 0.5 to 10 µm, more particularly 1 to 5 µm and even more particularly about 2 µm. The blurring of the captured raw image may negatively influence the resolution of the ophthalmoscope. Thus, the blurred images may be advantageously sorted out before subjecting them to further processing. The sorting out of the one or more of the captured raw images may comprise a frequency analysis of the captured raw image, wherein the absence of high frequencies except for the illumination pattern frequencies indicates that the respective raw image is blurred.

The method may further include a step of compensating aberrations of the wavefront of the fluorescent light emitted from the observed retinal region of the eye. The compensating of aberrations of the wavefront of the fluorescent light emitted from the observed retinal region of the eye may include detecting the wavefront aberrations and controlling a wavefront compensation component (such as for example a deformable mirror) to compensate at least partially for the detected wavefront aberrations. By advantageously employing wavefront compensation by means of adaptive optics in combination with structured illumination, the resolution may be further improved. Particularly in the field of ophthalmology, a compensation of wavefront aberrations may be advantageous, since the eye has itself an imperfect optical system with various aberrations.

It may further be advantageous to combine the method for non-invasive ophthalmoscopic fluorescence or reflection observations of the eyeground with axial tomography or other three-dimensional approaches, such as a three-dimensional approach (3D SMI) based on obtaining sets of images at different focal planes. Thereby, a three-dimensional image of the observed retinal region of the eye with improved resolution not only along the lateral direction, but also along the axial direction can be generated. This combination could for example be used to generate high resolution 3D images of the retinal region of the eye and deliver images comparable to a state of the art confocal microscope (~500 nm 3D resolution). It is also possible to combine the method for non-invasive ophthalmoscopic fluorescence observations of the eyeground with localization microscopy methods, without having to significantly change the optical layout of the employed microscope and/or increase its complexity.

In an example, the method may further include the steps of focusing the illumination pattern of illumination light in a plurality of different focal planes, for each focal plane obtaining a set of images including a plurality of images captured at a plurality of different relative positions of the specimen with respect to the illumination pattern projected onto the specimen, generating a three-dimensional image based on the obtained sets of images for the plurality of different focal planes.

When projecting the illumination pattern of illumination light onto the specimen (i.e. observed retinal region of the eye), the illumination pattern may be focused (or sharply displayed) in a focal plane. In case of a two-dimensional specimen/object, the focal plane generally coincides with the object plane and a plurality of images are captured for this one focal plane. These images are then processed in the manner described above to obtain a two-dimensional sub-resolution image.

In case of a three dimensional specimen/object (e.g. observed eye) the above procedure may be repeated for a plurality of different focal planes intersecting the specimen/object, thereby obtaining a plurality of images of different (thin) slices or layers of the specimen/object in the cross-sectional area of the specimen/object and the focal plane. For each focal plane a plurality of images is captured at a plurality of different relative positions of the specimen with respect to the illumination pattern projected onto the specimen. The captured images are further processed in order to generate a sub-resolution three-dimensional (3D) image. In particular, the plurality of images captured at each different focal plane may be processed to obtain a corresponding two-dimensional sub-resolution image of the respective cross-sectional area of the specimen in the manner described above, by advantageously using non-controlled relative movements of the specimen with respect to the illumination pattern. The obtained two-dimensional sub-resolution images may be then fused to form a three-dimensional image. An advantage of this approach is that the specimen/object does not need to be rotated. By processing of the obtained images captured at a plurality of different focal planes, an improved three-dimensional resolution may be achieved.

According to another aspect, there is provided an ophthalmoscope for non-invasive observations of the eye fundus. The ophthalmoscope may have a working distance, i.e. the distance between the at least one ophthalmoscope objective (objective system) and the observed retinal region of the eye, which is larger than 1 cm, particularly larger than 1 cm, more particularly larger than 2 cm, and even more particularly larger than 4 cm and in particular within the range of several centimeters (e.g. 1 cm to 10 cm), to allow the observation of the fundus in a patient or an animal without exerting undue pressure on the eye.

The ophthalmoscope includes a light source which emits illumination light. The light source may include one or more lasers (such as for example a diode pumped solid state laser), one or more light emitting diode(s) or any other suitable light source. The light source does not necessarily have to be a coherent light source. The light source may further include other optical elements, such as for example a collimator, etc.

The ophthalmoscope further includes a pattern generation system arranged in the optical path of the illumination light, the pattern generation system being configured to generate an illumination pattern of the illumination light. The pattern generation system may include one or more spatial light modulator(s) and/or diffraction grating(s) and/or an interferometer and/or other optical elements. The pattern generation system may for example be or comprise a two dimensional fixed grating or grid. In an example, the pattern generation system may be constituted by or include one or more spatial light modulators, such as micro-LCD spatial light modulator. The light source, the pattern generation system, the ophthalmoscope objective (or objective system comprising at least one objective) and optionally other optical elements (such as a collimator, an optical shutter, beam splitter(s), mirrors, filters, etc.) may constitute the illumination system of the ophthalmoscope.

The ophthalmoscope includes further at least one objective arranged and configured to illuminate the retinal region of the eye by projecting the illumination pattern onto the retinal region of the eye. In an embodiment the ophthalmoscope includes one objective through which the specimen/object is illuminated and/or reflected light or fluorescent light is detected. It is also possible to employ arrangements with two or more objectives, through which the specimen/object is detected and reflected light or fluorescent light is detected.

The at least one objective may include a focusing lens system which is configured to focus the illumination light in a way that the pattern structure shown in an image plane is imaged on the object plane in which the observed retinal region of the eye is located. Typically, the at least one objective includes a plurality of static and/or movable lenses, configured and arranged such as to reduce optical (including chromatic) aberrations. The plurality of lenses may constitute the focusing system of the objective. By varying the position of one or more of the movable lenses of the focusing system, the illumination pattern may be focused at different focal planes in the retinal region of the eye. Using different focal planes may be important in order to generate three dimensional images (3D-images).

In addition, the ophthalmoscope includes an image capturing system configured to detect at least a portion of fluorescent light emitted from the retinal region of the eye and/or to detect at least a portion of illumination light reflected from the retinal region of the eye, thereby capturing a plurality of images of the retinal region of the eye at a plurality of different relative positions of the retinal region of the eye with respect to the illumination pattern projected onto the retinal region of the eye. Between the capturing of at least two images of the series (for example between the capturing of each two consecutive images of the series) the relative position of the retinal region of the eye with respect to the illumination pattern projected onto the retinal region of the eye is shifted or varied in a non-controlled manner (e.g. stochastically). The non-controlled (stochastic) shift may be achieved by utilizing the saccadic movement of the eye in the manner explained above.

The image capturing system may include a camera configured and arranged such as to monitor the fluorescent light emitted from the retinal region of the eye. In particular, the camera may be a CCD camera. In an example, the image capturing may be synchronized with the image illumination in the manner described above. The ophthalmoscope and more specifically the illumination system may include a controller, particularly a micro-controller configured to synchronize the image capturing and the image illumination.

The ophthalmoscope further include a data processing system configured to process the series of captured images or respectively data obtained from the series of captured images, thereby producing a sub-resolution image of the retinal region of the eye. The data processing system may include a data storage, one or more processors and input/output terminals connecting the data processing system with the image capturing system and/or with a monitor or other suitable data output means. The captured images may be stored in the data storage, and the processor or the processing software may be configured to process the captured images by carrying out the processing methods as described above.

In particular, the processor may be configured to determine the shift of the relative position of the retinal region of the eye with respect to the illumination pattern projected onto the retinal region of the eye for each captured image in the series and to perform a-posteriori shifting of each captured image to reverse the corresponding stochastic shift of the retinal region of the eye with respect to the projected illumination pattern, thereby obtaining shifted images. Further, the processor may be configured to process the shifted raw images to extract a sub-resolution image of the retinal region of the eye, as described above.

Further, the data processing system (respectively the processor of the data processing system) may be configured to produce the sub-resolution image by applying frequency space based SMI reconstruction algorithms or other suitable reconstruction methods.

As discussed in connection with the method for non-invasive fluorescence observations of an eyeground using an ophthalmoscope, it may further be advantageous to combine the ophthalmoscope with axial tomography approaches. Thereby, a three-dimensional image of the observed retinal region of the eye with improved resolution not only along the lateral direction, but also along the axial direction can be generated. This combination could for example be used to generate high resolution 3D images of the retinal region of the eye and deliver images comparable to a state of the art confocal microscope (~500 nm 3D resolution). In addition, the ophthalmoscope may be combined with localization microscopy methods.

The ophthalmoscope may further include an eye movement detection device, such as a saccade detector, configured to detect the movement of the observed retinal region of the eye, and a controller configured to synchronize the image capturing and the image illumination with the detected movement.

The at least one objective, through which the retinal region of the eye is illuminated, is advantageously an objective having a low numerical aperture, for example less than 0.5. In particular, the at least one objective has advantageously a numerical aperture in the range of 0.1 to 0.5. Thereby, the working distance of the ophthalmoscope may be increased to a distance of up to several centimeters.

The relative position of the retinal region of the eye with respect to the illumination pattern projected onto the retinal region of the eye may be stochastically shifted or varied by utilizing stochastic saccades (i.e. the saccadic eye movements) of the eye and/or stochastic stage scanning and/or stochastic movement of a focusing lens system of at least one ophthalmoscope objective.

Advantageously, the inherent stochastic or quasi-stochastic movement of the eye itself, such as the saccadic eye movement, may be used in the ophthalmoscope for non-invasive fluorescence observations of a fundus. In case of letting the eye shift, i.e. in case of using saccadic eye movements, the illumination pattern may remain unchanged. In such case, a two-dimensional fixed grating may be used as pattern generation system.

Alternatively or in addition, the stochastic shift may be achieved by a stochastic stage scanning, i.e. a stochastic movement of the illumination pattern. For example, if the illumination pattern is produced by a spatial light modulator (such as a micro-LCD) the illumination pattern may be shifted or varied by means of the DVI port of a computer that drives a controller of the spatial light modulator. Alternatively or in addition, the stochastic shift of the relative position of the retinal region of the eye with respect to the illumination pattern may be achieved by a stochastic movement of a focusing lens system (particularly by a stochastic movement of at least one movable lens of the focusing lens system) of the at least one ophthalmoscope objective.

The ophthalmoscope may further include a pattern shifting component configured to stochastically vary the relative position of the specimen with respect to the illumination pattern projected onto the retinal region of the eye.

In particular, the pattern shifting component may be configured to perform a stochastic stage scanning and/or to stochastically move the focusing lens system of the at least one objective. In case the intrinsic periodic or non-periodic movement of the eye itself (particularly the saccadic eye movement) is used to stochastically vary the relative position of the retinal region of the eye with respect to the illumination pattern, the ophthalmoscope might not necessarily require a dedicated pattern shifting component. It is of course possible to employ a dedicated pattern shifting component in addition to utilizing the saccadic movement of the eye.

Alternatively or in addition, the pattern shifting component may be configured to shift the illumination pattern within an image plane. For example, the pattern shifting component may include a programmable spatial light modulator and a pattern controller configured to control the spatial light modulator, for example by controlling and/or shifting the pattern displayed on it. In another example, the pattern shifting component may include a non-programmable or permanent/fixed diffraction grating or spatial light modulator. In this case, the pattern shifting component may include a movable stage configured to move or translate the diffraction grating or the spatial light modulator in the image plane (i.e. a plane substantially orthogonal to the axis or direction of propagation of the illumination light) and optionally in the direction orthogonal to the image plane.

In a further example, the pattern shifting component may include one or more optical elements, such as mirrors, deflectors, etc., configured to scan the generated illumination pattern over the object plane.

Still further alternatively or in addition, the pattern shifting component may be configured to move or translate the focusing lens system (or at least one movable lens of the focusing lens system) of the at least one ophthalmoscope objective along the optical axis of the ophthalmoscope/objective and and/or in a plane orthogonal to the optical axis.

The light source of the ophthalmoscope may be configured to emit stroboscopic illumination light having on- and off-times, wherein the retinal region of the eye is illuminated only during the on-times, and wherein the on-times are respectively shorter than the off-times during which the illumination of the retinal region of the eye is interrupted. Thus, the overall illumination time of the eye can be reduced and damage of the eye prevented.

The light source may for example include a shutter (e.g. a mechanical or electro-optical shutter) and/or an acousto-optic modulator, configured to switch on and off the illumination light. Alternatively, the ophthalmoscope may include one or more optical components (such as digital mirror(s)) configured to divert the illumination light away from the observed eye during the off-times.

The ophthalmoscope may further include a wavefront compensator arranged in an image detection arm or path of the ophthalmoscope configured to compensate for optical aberrations, in particular diffraction aberrations. The wavefront compensator (including, for example, a deformable mirror and/or other adaptive optics elements) may be located in a conjugate eye-lens plane The wavefront compensator may be adjusted iteratively by analyzing the fluorescence and/or reflection image of the retinal region of the eye (i.e. the image of the retinal region of the eye obtained by detecting at least a portion of the emitted fluorescent light and/or by detecting at least a portion of the reflected light) or the reflection image of the specimen (i.e. the image of the specimen obtained by detecting at least a portion of the reflected illumination light). Alternatively or additionally, the wavefront compensator may be adjusted iteratively by analyzing an image of the retinal region of the eye of scattered/reflected light from an additional light source (e.g. an infrared laser or LED). The wavefront compensator may further include a wavefront sensor (such as a Shack-Hartmann sensor) configured to detect and/or analyze the aberrations in the emitted or reflected light from the retinal region of the eye.

The illumination and image acquisition may advantageously be triggered shortly after a stochastic shift of the relative position of the retinal region of the eye with respect to the illumination pattern projected onto the retinal region of the eye, particularly after a saccadic movement of the eye. The trigger signal could be given by a suitable variation or shift detector, particularly a high speed saccade detection device. By the application of such an additional device, the number of redundant and faulty detected images can be reduced.

Accordingly, the ophthalmoscope may further include a shift detector for detecting stochastic shifts of the relative position of the retinal region of the eye with respect to the illumination pattern projected onto the retinal region of the eye, and a synchronizer configured to synchronize the illumination of the retinal region of the eye and/or the capturing a series of raw images with the detected stochastic shifts of the relative position of the retinal region of the eye with respect to the illumination pattern projected onto the retinal region of the eye.

The shift detector may include for example one or more high-speed photodetectors (such as photodiodes) and an eye movement determination component configured to detect/calculate the saccadic eye movement from the signal (modulated photocurrent) produced by the high speed photodetector. The synchronizer may include for example a controller (such as micro-controller) configured to output a synchronization signal to the illumination system (such as outputting a synchronization signal to a laser and/or a shutter, a beam deflector or other optical components included in the illumination system of the ophthalmoscope) and to the image capturing system and in particular to the camera.

By the employment of a shift detector and a synchronizer, the illumination of the retinal region of the eye may be synchronized with the detected stochastic shifts of the relative position of the retinal region of the eye with respect to the illumination pattern projected onto the retinal region of the eye. Thereby, the overall illumination time of the eye can be reduced and the eye can be prevented from damage.

The ophthalmoscope may further include a collimator to collimate the illumination light. The collimator may be positioned in front of the pattern generation system, i.e. in the optical path of the illumination light emitted by the light source. The collimator may be an adjustable collimator, with the help of which the size of the illuminated field may be adjusted.

The ophthalmoscope may further include one or more beam splitter configured to separate the illumination light illuminating the retinal region of the eye from the fluorescent light emitted from the illuminated retinal region of the eye and/or the illumination light reflected from the illuminated retinal region of the eye. In case of non-invasive reflection observations, the beam splitter may have for example a reflection-to-transmission ratio of R/T=0.1. In case of non-invasive fluorescence observations, the beam splitter may be a dichromatic beam splitter. The beam splitter (e.g. a dichromatic beam splitter) may be arranged such that the illumination pattern of illumination light produced by the pattern generation system is imaged at the back focal plane of the at least one objective by a reflection on the beam splitter or through the beam splitter. In particular, the beam splitter may be positioned in the observation/image detection path of the ophthalmoscope between the at least one objective and the image capturing system.

The ophthalmoscope may further include a filter arranged in front of the image capturing system and configured to transmit fluorescent light and/or reflected light and to block remaining illumination light (e.g. excitation light).

The pattern generation system may include an intensity modulating light transmitting spatial light modulator for spatially modulating the intensity of the illumination light.

The intensity modulating light transmitting spatial light modulator may be a micro liquid crystal display (micro-LCD), such as for example used in mass produced light projectors. The micro-LCD may display a pattern or a structure in an image plane perpendicular to the optical path of the ophthalmoscope. Thus, the illumination light transmitting the micro-LCD may be spatially modulated in its intensity by the displayed pattern or structure in the image plane. The intensity modulating light transmitting spatial light modulator (for example a micro-LCD) may include a controller which may be driven by the DVI port of a computer. Thereby, the displayed pattern or structure may be controlled.

Instead of or in addition to the micro-LCD, an interferometer or a conventional optical grid (particularly a fixed two-dimensional grating) may be used to generate the illumination pattern of illumination light. It is of course also possible to employ an intensity modulating light reflecting spatial light modulator or other types of spatial light modulators.

According to another aspect, there is provided a computer implemented method for generating sub-resolution images of a fundus based on a series of images of the retinal region of the eye obtained by an ophthalmoscope, wherein the series of images is obtained by projecting an illumination pattern of illumination light onto the retinal region of the eye, thereby illuminating the retinal region of the eye, detecting at least a portion of fluorescent light emitted from the retinal region of the eye, thereby capturing a series of images at a plurality of different relative positions of the retinal region of the eye with respect to the illumination pattern projected onto the retinal region of the eye, wherein between the capturing of at least two images of the series (e.g. of each two consecutive images of the series) the relative position of the retinal region of the eye with respect to the illumination pattern projected onto the retinal region of the eye is stochastically varied or shifted, the method including the steps of receiving said series of raw images of the retinal region of the eye, for each received image determining the non-controlled shift of the relative position of the retinal region of the eye with respect to the illumination pattern projected onto the retinal region of the eye, a-posteriori shifting of each received image to reverse the corresponding non-controlled (e.g. stochastic) shift of the retinal region of the eye with respect to the projected illumination pattern, thereby obtaining a corresponding shifted image, and processing the shifted images to extract a sub-resolution image.

The determining of the non-controlled shift of the relative position of the retinal region of the eye with respect to the illumination pattern projected onto the retinal region of the eye, the a-posteriori shifting of each received image and the processing of the shifted images may be carried out as described above in connection with the method for non-invasive fluorescence observations of a fundus using an ophthalmoscope.

According to yet another aspect, a computer program product, which, when loaded into the memory of a computer and executed by the computer may perform the above computer implemented method. The computer program product may be tangibly embodied in an information carrier.

A schematic representation of a fluorescent microscope (a large distance nanoscope or LDN) according to an example is shown in FIG. 1A. The shown large distance nanoscope may be used as a (high resolution) ophthalmoscope.

Optical Arrangement

In this example, band limited fluorescence excitation light is generated by a light source 10. The light source 10 includes a laser 1, a laser shutter 3 and a collimator 5. The laser may be a diode pumped solid state laser (DPSS laser) with 532 nm wavelength and 800 mW light power. The light source does not necessarily have to emit coherent light if a kind of diffraction grating is used as it is the case with the micro-LCD 13. Instead of using shutter, it is possible to use a pulsed laser. For example, the laser current may be directly modulated by a TTL (Transistor-Transistor Logic), thereby switching the laser 1 on and off.

The light may be activated and de-activated in a ms timeframe. This may be done by means of a mechanic shutter 3 arranged in the direct laser beam after the laser head. The illumination timeframes may be in the order to 10 ms and the times between in the order of roughly 100 ms. The light emitted from the laser 1 is collimated by a collimator 5 and directed into a pattern generation system 20. The pattern generation system 20 includes an intensity modulating light transmitting spatial light modulator. In the example shown in FIGS. 1A and 1B, the pattern generation system is constituted by a micro-LCD 13, such as for example a micro-LCD used in mass produced light projectors. The micro-LCD 13 includes at least two polarizers and a controller (not shown in FIGS. 1A and 1B) which may be driven by the DVI port of a computer/processor that drives the setup. The same computer/processor may also perform the processing of the captured images to obtain a sub-resolution image as described above. It is also possible to use a conventional, fixed diffraction grating (for example a two-dimensional diffraction grating) or a combination of several (for example three) diffraction gratings with different orientations and/or periods.

The pattern generator system (here: constituted by a micro-LCD 13) is positioned in the illumination path of the large distance microscope between the collimator 5 and a dichromatic (dichroic) beam splitter 30. The image displayed on the micro-LCD 13 (i.e. the image displayed in the image plane) is projected onto the specimen. After passing through the pattern generator system 20, the patterned excitation light is deflected by the dichromatic beam splitter 30 that is reflective for the excitation light and transmissive for the fluorescence emission light. It is also possible to use a chromatic beam splitter having inverted properties, i.e. a dichromatic beam splitter which is transmissive for excitation light and reflective for fluorescence emission light.

The excitation light passes through a large working distance objective lens (microscope objective or objective) 40 having a numerical aperture of less than 0.5, for example in the range of 0.1 to 0.5. The objective lens 40 may be constituted by a single lens or include a system of lenses (hereinafter also referred to as a focusing system). For example the objective 40 may include one or more fixed focusing lenses and one or more movable (variable) focusing lenses. The focal length of the objective may be fixed or variable. By varying the focal length, different focal planes may be obtained, which enable, for example, the generation of 3D-images.

Depending on the application, the microscope may comprise one or more (e.g. two or three) objectives. For example, more than one objective may be advantageously used for investigating tissue samples.

The working distance may be between several millimeters to several centimeters.

The excitation light is focused by the objective lens (objective) 40 in a way that the displayed pattern on the micro-LCD 13 is imaged in the object plane 50. Because of the nature of imaging systems, only a limited bandwidth of information from the pattern generator system 20 (here the micro-LCD) is transferred to the object plane. Typically, the pattern displayed on the micro-LCD 13 is periodic and only the zero and the plus and minus first orders of diffraction are transmitted into the object plane 50. The higher orders are blocked by additional or existing (e.g. the back side lens of the objective) apertures. It could also be beneficial to block out or to weaken the zero order beam.

In the specimen, fluorochromes may be located. Therefore, fluorescence takes place in the object plane 50. Under relatively low illumination conditions (e.g. in the order of 1 W/cm2, where no noticeable saturation effects occur) as used according to the present example, the fluorescence is linear to the intensity of the excitation pattern projected into the object plane 50. At least a fraction of the emitted fluorescence light is collected by the objective lens 40. This light passes through the focusing system of the objective lens 40 and the dichromatic beam splitter 30, then passes an optional additional blocking filter 60 and finally enters the imaging system 70 which may include a CCD camera 72. The blocking filter 60 is used to block out remaining excitation light that passes the dichromatic beam splitter 30 since the excitation light intensity surpasses the fluorescence emission intensity by orders of magnitudes. The image sensor of the imaging system is located in an image plane, which means that light from a point in the object plane 50 is focused on a diffraction limited spot on the sensor. The distance between the image sensor and the object plane 50 may be substantially equal to the distance between the object plane 50 and the micro-LCD 13.

The specimen may be fluorescently labeled by suitable fluorescent dyes or markers. It is also possible to utilize the fluorescence from substances which are naturally present in a given specimen. This for example, if the specimen is an eye, naturally autofluorescent lipofuscin is located in the retinal pigment epithelium Alternatively or additionally, specific regions (e.g. blood vessels) in the back of the eye may be labeled by suitable fluorescent labels (for example fluorescein).

Figure 1B:
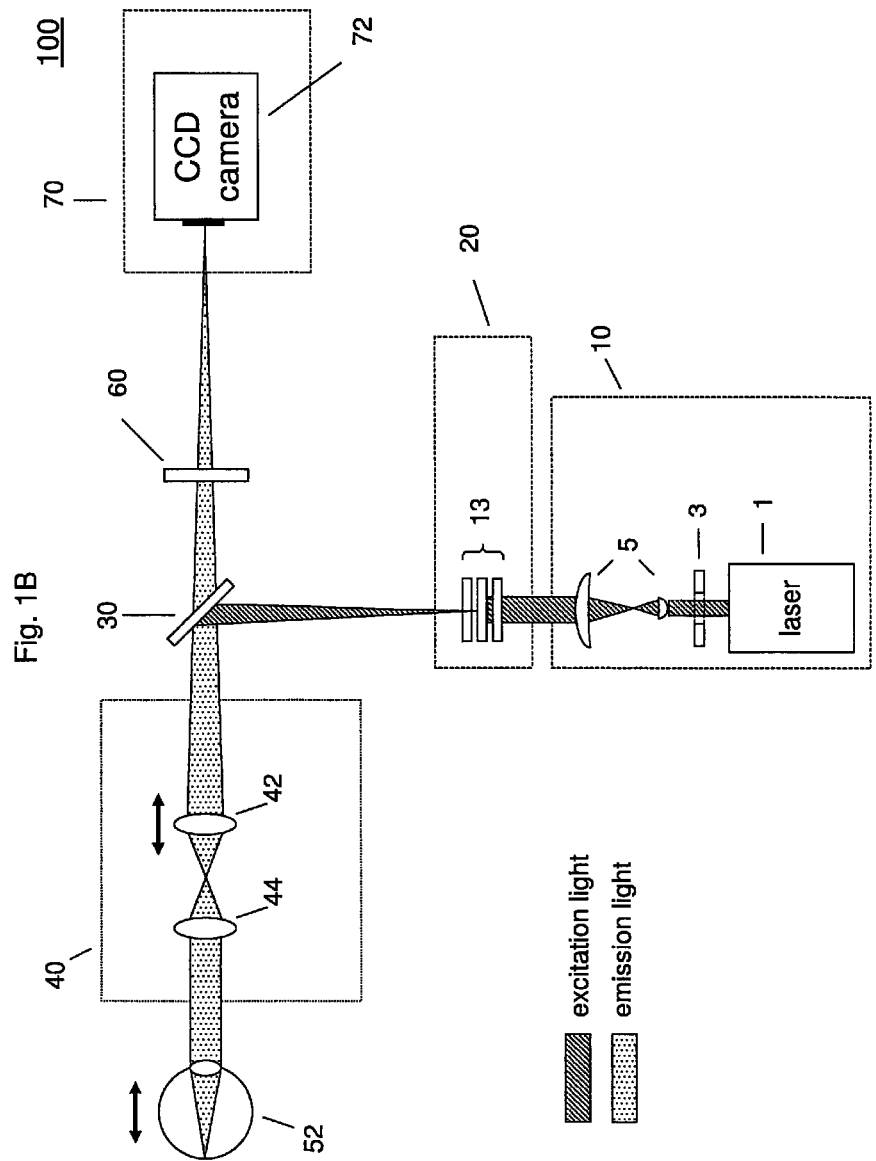
FIG. 1B shows a schematic representation of an optical arrangement of an ophthalmoscope according to another example.

FIG. 1B shows a schematic representation of an ophthalmoscope as an example of a fluorescent microscope (a large distance nanoscope or LDN) for an application for eye examinations (observations). In this example the objective comprises a fixed focusing lens 44 and a movable (variable) focusing lens 42. The variable lens 42 may be moved or translated in particular along the optical axis of the microscope/objective. Both lenses 42 and 44 may be movable lenses. Thus, the focal depth of the lens system/objective may be made variable. The observed specimen in this case is a patient's eye 52. The remaining elements of the large distance microscope are substantially the same as the corresponding elements of the example shown in FIG. 1A, so that a detailed description thereof will be omitted.

The ophthalmoscope may advantageously use the stochastic or quasi-stochastic saccadic eye movements to realize a stochastically variation or shift of the relative position of the observed specimen (the eye) with respect to the illumination pattern. If the eye is fixed (e.g. due to paralysis of the eye muscles and/or use of fixation brackets), the illumination pattern may be stochastically shifted instead of leaving the pattern unchanged and letting the specimen (for example eye) shift. This may be done for example by varying the pattern displayed on the programmable spatial light modulator (such as micro-LCD) or by other appropriate means. The change of the displayed pattern may be conducted during the off-times.

The eye as an optical system has various aberration, including diffraction aberrations, strong enough to limit the resolution power. The employment of a structured/pattern illumination may reduce this problem because object information may be shifted into a region close to the center of the eye lens that is less affected by aberrations. However, it might be beneficial to use adaptive optics to compensate the diffraction aberrations of the eye. For example, a wavefront compensator (not shown in FIGS. 1A and 1B) may be located in a conjugate eye-lens plane. The wavefront compensator may be for example a deformable mirror. The wavefront compensator may be adjusted iteratively by analyzing the fluorescence image or an image of the fundus of scattered light from an additional (secondary) light source, such as an additional infrared laser or LED. Another possibility may be to use the wavefront sensor to analyze the aberrations in the reflected light (fluorescence excitation or secondary light source).

Next, the data acquisition and data processing using an exemplary large distance microscope (or, for example, ophthalmoscope) will be described in more detail:

In the following, it is considered that the specimen shifts in a non-controlled (i.e. undetermined or involuntary) manner, e.g. stochastically or quasi-stochastically. However, it is also possible to stochastically shift the illumination pattern, instead of the specimen or to shift both the specimen and the illumination pattern.

In an example stroboscopic illumination and image acquisition may be utilized. The camera 72 and the illumination system, which may include the light source 10, the pattern generation system 20, the dichromatic beam splitter 30 and the objective 40, may be set up in a way that the excitation light is only projected onto the specimen when the camera 72 is acquiring (said on-time). When the CCD camera 72 reads out, the excitation beam is toggled off or switched-off (said off-time). This may be accomplished by an application of a high speed (for example <1 ms transfer time) mechanic shutter. To achieve much higher transfer times, an acousto-optic modulator or other high-speed optical shutter may be used instead of a mechanical shutter. In addition or alternatively an inherently pulsed (e.g. a pulsed laser) or quickly activatable and de-activatable (e.g. an LED) light source could be used. The shutter 3 and the camera 72 may be triggered by a micro-controller.

Instead of using stroboscopic illumination, it is also possible to use continuous illumination, in particular in combination with a high-sensitive, high-speed camera with rapid read-out time.

The illumination timeframes may be much shorter than the timeframes between two successive illuminations. Thus, the distance the specimen moves during the on-time (image acquiring time) is much shorter than the moving distance that occurs during the off-time. If for example, the observed specimen is an eye, the probability for a saccadic eye movement during the illumination timeframes is low, whereas the probability for eye movement during the off-time is higher. In an example, the illumination pattern is substantially constant during the image acquisition, whereas the specimen moves between the single images. In one image acquisition cycle an amount of 3 to 100 raw images may be taken. If the quasi-stochastic movement during a certain on-time is extraordinarily large, i.e. if it exceeds a certain threshold larger than 2 µm, the according image might be blurred. The blurred images can be sorted out by the use of a frequency analysis. When high spatial frequencies (in the range of 1/(2 µm)) in the image, except for the illumination pattern frequencies, are absent, the according raw image is blurred due to strong movements of the sample and can therefore be neglected.

After the image acquisition, the single images are shifted to reverse the sample movement a-posteriori. This can be accomplished by first frequency filtering the images to remove the primary illumination pattern information from the images and afterwards shifting the images iteratively. Other, more sophisticated approaches could be applied to do this.

When the images $I_i$ are shifted back by the shifting vector $\vec{v}_i$, the illumination pattern is shifted by the shifting vector relatively to the now constant image which corresponds to a pattern with a phase ϕ relatively to the original pattern. The phase ϕ is given by $$\varphi = \frac{\mathrm{mod}(\vec{n}_{mod} * \vec{v}_i, P)}{P} * 2\pi, \quad (19)$$

with the unit vector in the direction of illumination pattern modulation $\vec{n}_{mod}$ and the illumination pattern period P.

The shifting vector $\vec{v}_i$, may be determined for example by applying analytical deconvolution and determining the position of the maximum of the intensity of the deconvolved image in the manner described above.

Conventional frequency space based structured excitation illumination (SEI) reconstruction software as described in the publication R. Heintzmann et al., "Laterally modulated excitation microscopy: Improvement of resolution by using a diffraction grating", proceedings of SPIE (1999), 3568, 185, or other suitable reconstruction methods can be applied in order to extract high resolution images.

This results at least in a twofold higher resolution in the direction of the illumination pattern modulation. Further, the optical sectioning is greatly improved by the image reconstruction.

To obtain an isotropic resolution improvement in the lateral plane (the plane orthogonal to the beam path), the procedure may be repeated with rotated illumination patterns (e.g. patterns at 0°, 60°, 120°). This may be achieved by displaying a rotated pattern on the LCD. Alternatively, a two-dimensional pattern that contains several gratings with different orientations in the image plane where the micro-LCD is located may be employed. In this case, a solid, fixed gating can be used. For each angle orientation of the illumination pattern, a plurality of images may be captured at different relative positions of the illumination pattern projected onto the specimen with respect to the specimen, the different relative positions being shifted with respect to each other or with respect to a reference position in an uncontrolled, for example stochastic manner. The plurality of images may be subjected to an image processing to obtain a high resolution image in the manner described above.

If the specimen is fixed, shifts are not disrupting the image quality in certain images on the one hand and cannot be applied for shifting the relative position of the specimen with respect to the illumination pattern projected onto the specimen on the other hand. In this case, the illumination pattern may be moved instead of leaving the pattern unchanged and letting the specimen shift. In an example, this can be done by displaying a shifted pattern on the micro-LCD. This change in pattern is conducted during the off-times.

Next a further example of an ophthalmoscope employing a combination with fluorescence tomography will be explained in more detail:

The resolution of an optical system is limited by the numerical aperture (NA) given by $$NA = n*\sin(a)$$

with the refractive index n and the half opening angle of the objective lens. The resolution (i.e. the smallest resolvable distance) in the lateral direction (in the lateral plane, i.e. the plane perpendicular to the light path) is inversely proportional to the numerical aperture NA. In the axial direction along the light path, however, the resolution is inversely proportional to the square of the numerical aperture NA. For a given objective lens diameter, a doubled working distance (i.e. distance between specimen and objective lens) leads to roughly (small angle approximation) a doubled resolvable distance along the lateral direction but a fourfold resolvable distance along the axial direction (i.e. to a twofold and fourfold increase of the resolvable distance along the lateral and axial direction respectively).

For large (for example larger than 1 cm) working distances this usually leads to very low resolutions in the axial direction that are orders of magnitude worse than the corresponding resolution along the lateral directions. This fact essentially renders 3D-imaging useless for large working distance conventional fluorescence microscopy. Structured excitation illumination (SEI) doubles the resolution in the lateral direction as wells as in the axial direction, however, the non-proportionality remains.

To improve the axial resolution in fluorescence imaging, axial-tomography has been developed (see for example the publication Heintzmann and Cremer, "Axial tomographic confocal fluorescence microscopy", Journal of Microscopy, 206(1), 2002, pp. 7 to 23). The specimen is located on an apparatus that can be rotated along an axis perpendicular to the beam path (e.g. a glass fiber, a glass tube). With this apparatus the specimen is rotated to different angles and respectively imaged in 3D. Afterwards, by rotating, shifting and re-sampling of the dataset and consecutively applying a multi point spread function (multi-PSF) deconvolution, a 3D image can be generated that has at least the resolution of the raw images along the lateral direction, but in 3D along the axial direction as well.

In an example the method for obtaining a sub-resolution image of a specimen by projecting an illumination pattern of excitation light or in other words structured excitation illumination may be combined with axial tomography. This may be achieved by rotating the specimen along an axis perpendicular to the optical axis of the microscope to a plurality of rotation angles and at each rotation angle obtaining a set (rotation dataset) of raw images including a plurality of raw images captured at a plurality of different relative positions of the specimen with respect to the illumination pattern projected onto the specimen.

Each rotation dataset may be processed with conventional Fourier space based structured excitation illumination reconstruction methods. Subsequently, a deconvolution approach of fluorescence tomography may be used for the improvement of axial resolution and generating a three-dimensional image. Alternatively, a multi-PSF deconvolution approach can be used to process conventional structured excitation illumination data after a resorting of the image data. Therefore all the raw data could first be resorted and afterwards processed by a multi-PSF deconvolution algorithm. This approach could for example be used to generate high resolution 3D images of eye tissue samples or using animal models and deliver images comparable to a state of the art confocal microscope (~500 nm 3D resolution). Here the stochastic movement of the specimen could also be used for phase shifting of the illumination pattern relative to the specimen.

In another example a three-dimensional image may be obtained by recording sets of images taken at different focal planes in the manner described above. Each obtained set of images (dataset) comprises a plurality of images captured at different relevant positions of the observed retinal region with respect to the illumination pattern. The obtained sets of images for different focal planes may be then processed with various reconstruction techniques to obtain a sub-resolution three-dimensional image. Thus rotation of the observed specimen (the retinal region of the eye) may be avoided.

Figure 2:
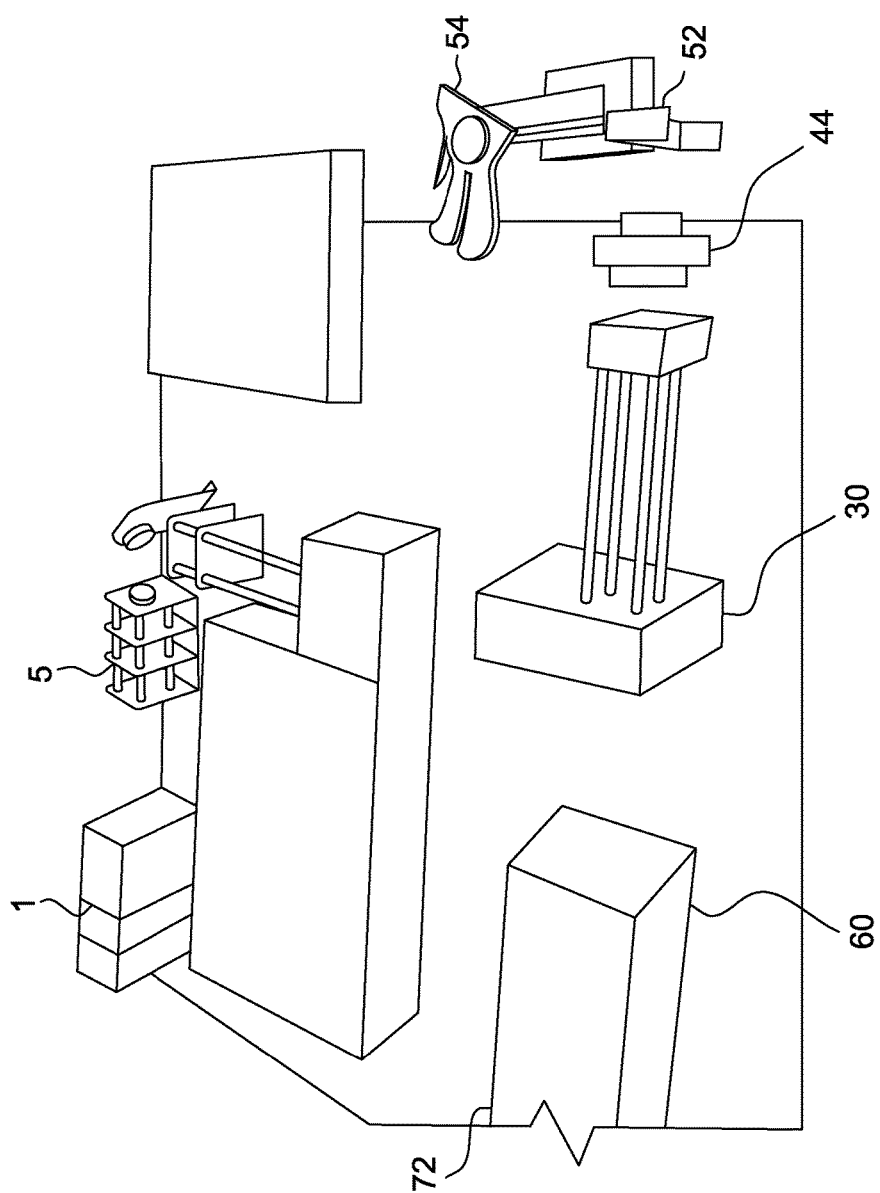
FIG. 2 shows a photograph of an optical arrangement of an ophthalmoscope according to one example.

FIG. 2 is a photograph of an exemplary optical arrangement of a large distance microscope (for an application as an ophthalmoscope) according to the example shown in FIG. 1B. In particular, FIG. 2 shows a light source 10 including a laser 1 and a collimator 5, a pattern generation system 20 (here: a micro-LCD 13), a chromatic beam splitter 30, a blocking filter 60 and an image capturing system comprising a CCD camera 72. Moreover, a focusing lens system comprising a movable lens 42 and a fixed lens 44 forms the objective of the microscope. The specimen of FIG. 2 is a test eye 52 which is mounted on a specimen mounting apparatus 54.

The test eye (test sample or test specimen) consists of a fixated human retinal pigment epithelium tissue imbedded between two cover slips and fixed on the inner back of an artificial test eye model. The artificial test eye model consists basically of a single lens with focal length and aperture corresponding to the focal length and aperture of a human eye.

Figure 3B:
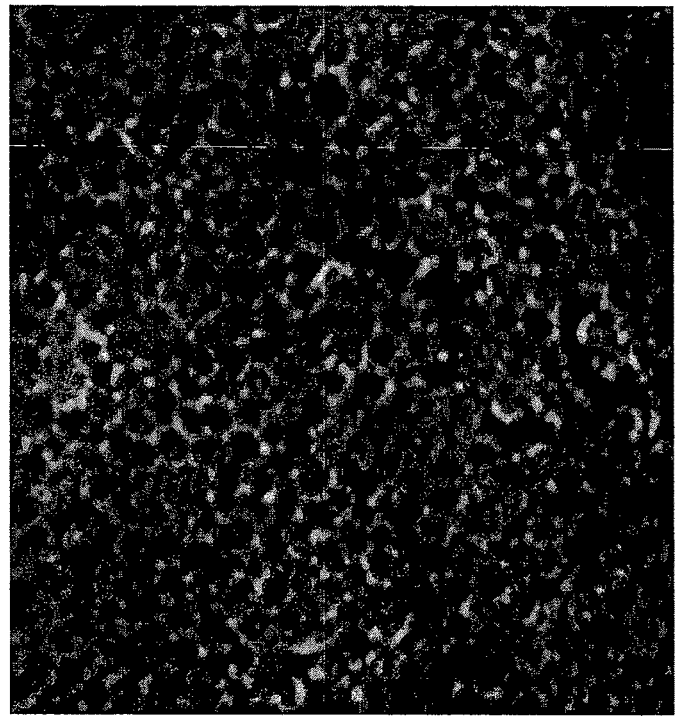

FIGS. 3A and 3B show two microscope images of the inner back of a test eye, wherein the first image (FIG. 3A) has been obtained by a conventional microscope and the second image (FIG. 3B) has been obtained by a large distance nanoscope using structured illumination according to an example. As evident upon a comparison of the two images, the second image (FIG. 3B) has a considerably improved resolution and contrast. To produce the conventional microscope image (FIG. 3A), the non-invasive ophthalmoscope has been used in the homogeneous illumination mode, i.e. without structured illumination.

The resolution of the large distance microscope and in particular the ophthalmoscope according to an example may be as high as several micrometers (which is about twice as high than in conventional systems with the same numerical aperture). In particular, by employing a large distance microscope using structured illumination according to an example, it is possible to distinguish single cells.

In an example, the large distance microscope (LDN or large distance nanoscope) may be used for observing the eye fundus. In this example the saccadic movement of the eye may be advantageously used to achieve the stochastic shift of the relative position of the specimen (the observed eye) with respect to the illumination pattern. As the saccadic movement is quasi-periodic, it may be beneficial to trigger illumination and image acquisition shortly after a saccade. The trigger signal could be given by a high speed saccade detection device. In order to achieve the necessary high speed and sensitivity, the state of the art solutions might not be fast enough. Therefore, a different approach according to FIG. 4 may be used.

FIG. 4 is a schematic view of a saccade detection device (as an example of a specimen movement detection device) which works with reflected light (e.g. reflected at the eye surface). The saccade detection device includes a high speed light- or photo-detector 90 (e.g. a photo diode). In particular, the specimen 52 (in this example an eye) may be illuminated by an additional, slightly focused and coherent laser light 80 (different from the excitation light) which is reflected at the specimen's surface 53. Since the eye surface is not perfectly spherical, the wavefront of the laser light 81 changes upon reflection at the eye surface. Hence, the angle of reflection of the reflected light varies with the position of the eye. Additionally, because of the distortion of the wavefront which is induced by the non-spherical surface of the eye, the reflected light will interfere to generate an inhomogeneous intensity distribution in distance (greater than several cm) of the eye surface, wherein a change or modulation of the inhomogeneous intensity distribution indicates a saccadic movement. In FIG. 4, the wavefront of the laser light after reflection at the eye surface is indicated by the reference number 83. A high speed photo-detector detects the intensity distribution of the reflected laser light 82, i.e. the reflected light interference intensity profile 85 (also referred to as "speckles") by measuring a corresponding photo current. The intensity distribution depends on the position of reflection on the eye surface. Thus, when the eye performs a saccadic movement, the intensity distribution changes or modulates. The saccade detection device includes further a saccadic eye movement determination component 95 configured to detect/calculate the high speed intensity modulation and thus the saccadic eye movement from the signal (modulated photocurrent) produced by the high speed photo-detector 90. The illumination of the specimen 52 with patterned excitation light and/or the image acquisition may be then synchronized with the specimen's (in this case eye's) movement. By employing an additional saccade detection device, the number of redundant and faulty raw images may be reduced.

Figure 5:
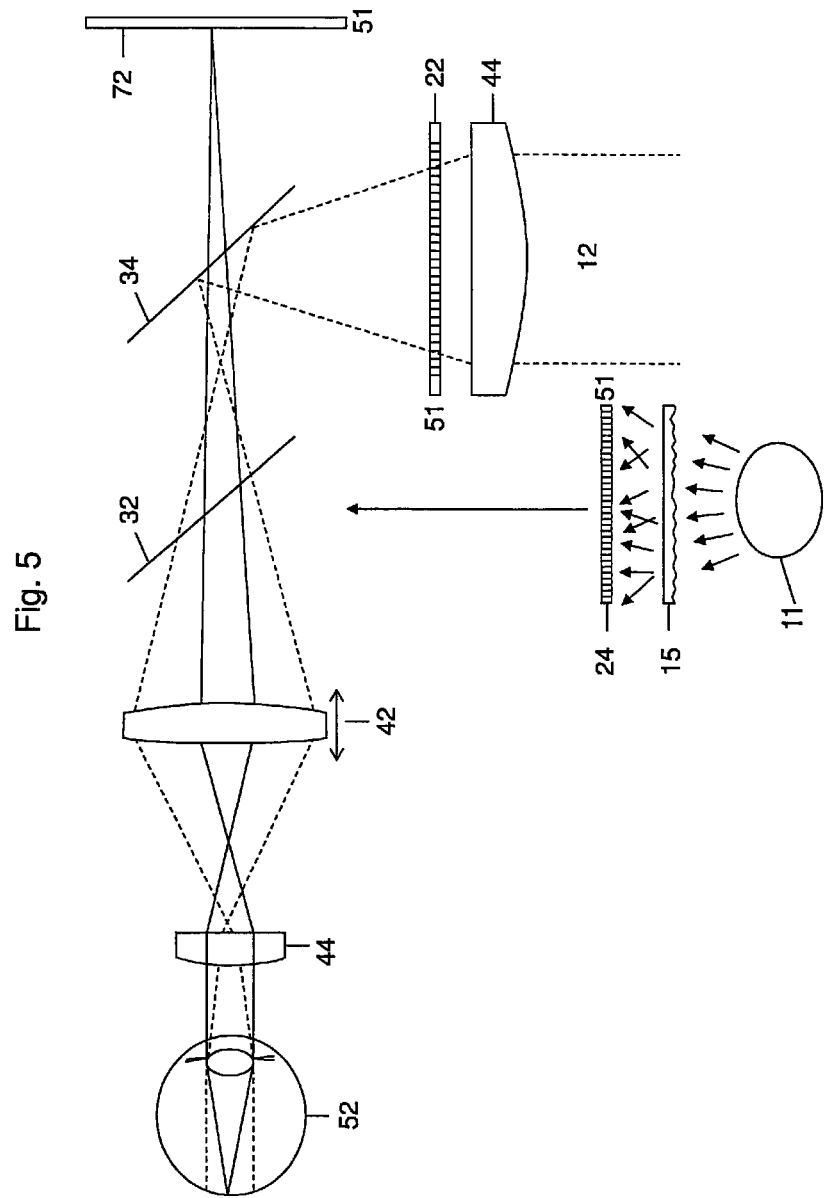
FIG. 5 is a schematic representation of an optical arrangement of an ophthalmoscope according to still another example.

FIG. 5 shows a schematic representation of the optical arrangement of an ophthalmoscope (as an example of a fluorescent and/or reflection microscope for an application for eye examinations or observations), which may be operated in a fluorescence mode, in a reflection mode or in a combination thereof. In this example, a fixed focusing lens 44, a movable (variable) focusing lens 42 and a CCD camera 72 are similar to FIGS. 1A and 1B, so that a detailed description thereof will be omitted. As in FIG. 1B, the observed specimen is a patient's eye 52. Reference sign 51 indicates the image planes in FIG. 5.

With respect to the fluorescence mode, the specimen (e.g. the retinal region of the eye 52) is illuminated by projecting an illumination pattern of excitation light onto the specimen (e.g. the retinal region of the eye). The illumination pattern of excitation light is generated by a light source 12 which emits excitation light in order to pass through a lens 8 and a pattern generation system 22. The excitation light has a wavelength suitable to excite the fluorochromes located in the specimen (e.g. the retinal region of the eye 52). The pattern generation system 22 includes an intensity modulating light transmitting spatial light modulator (e.g. a micro-LCD or a diffraction grating). After passing through the pattern generator system 22, the patterned excitation light is deflected by the dichromatic beam splitter 34 that is reflective for the excitation light and transmissive for the fluorescence emission light. It is also possible to use a chromatic beam splitter having inverted properties, i.e. a dichromatic beam splitter which is transmissive for excitation light and reflective for fluorescence emission light.

With respect to the reflection mode, the specimen (e.g. the retinal region of the eye 52) is illuminated by projecting an illumination pattern of illumination light onto the specimen (e.g. the retinal region of the eye). The illumination pattern of illumination light is generated by a light source 11 which emits illumination light in order to pass through a diffuser 15 and a pattern generation system 24. The pattern generation system 24 includes an intensity modulating light transmitting spatial light modulator (e.g. a micro-LCD or a diffraction grating). After passing through the pattern generator system 24, the patterned illumination light is deflected by the beam splitter 32 which may be characterized by a reflection to transmission ratio of R/T=0.1, i.e. the dichromatic beam splitter 32 may be configured to only reflect 10% of the total amount of illumination light.

With respect to a combination of fluorescence mode and reflection mode, an optical switch (not shown in FIG. 5) may be used to either illuminate the specimen by means of light source 12, lens 44, pattern generation system 22 and dichromatic beam splitter 34 or by means of light source 11, diffuser 15, pattern generation system 24 and beam splitter 32. The optical switch may be realized by using polarizers and analyzers.

FIGS. 6A-6F are schematic illustrations of the determination of the non-controlled (e.g. stochastic/random) shift of the relative position of the specimen (e.g. an eye) with respect to the illumination pattern projected onto the specimen. FIG. 6A shows an example of an unshifted object having a fluorophore distribution $\rho_0(x)$. This object may be shifted in a non-controlled manner (in case of an eye, due to stochastic/random saccadic movements), thereby varying its position as illustrated by FIG. 6B. The fluorophore distribution of the shifted object (specimen) is given by $\rho_1(x)=\rho_0(x-\Delta x)=\rho_0(x)*\delta(x-\Delta x)$ (see equation 3 above), where $\Delta x$ is the shift vector with respect to the unshifted object. By projecting an illumination pattern $I_{Illu}(x)$ (exemplarily shown in FIG. 6C) onto the object, two images, namely the image $Im_0(x)$ of the unshifted illuminated object (FIG. 6D) and the image $Im_1(x)$ of the shifted illuminated object (FIG. 6E), may be captured. As illustrated in FIG. 6F, the shift vector $\Delta x$ may be obtained by determining the position of the peak P (i.e. the maximum) of the analytic deconvolution $R(x)$ (see equations 15 to 18 above), which results from the delta function $\delta(x-\Delta x)$ being contained in the analytic deconvolution $R(x)$ (see equation 18 above).

Further exemplary methods and apparatuses for obtaining a sub-resolution image of a specimen may include one or more of the following features: The illumination pattern may be realized by spatially modulating illumination intensity. The illumination pattern (e.g. a periodic illumination pattern) may be moved during the exposure and single images may be taken at different positions of the excitation pattern on the specimen. Subsequently, the received data may be processed further by using a general purpose or a dedicated computer or a computer system in order to obtain high resolved images.

In an example, by means of a transmitting liquid crystal array (micro-LCD display) arranged in the optical path of the excitation light, a grid is projected to the specimen. The optics is configured and arranged such that the LCD is located in an intermediate image plane of the object plane. The fluorescence distribution in the object plane, excited by the excitation pattern, is imaged on a camera which is also located in an intermediate image plane. A pattern (for example a fringe pattern or a grid) is displayed on the display. Optionally, the displayed pattern can be shifted and changed arbitrarily. Images are taken at different positions of the illumination pattern. For this purpose, the pattern may be shifted between the expositions. This can be done by either a shift of the whole or a part of the apparatus with respect to the specimen, or by a shift of the grid displayed on the display. It may also be possible to generate the grid by other means, for example by means of an interferometer.

In general, in an embodiment intrinsic or externally caused periodic or non-periodic or non-controlled (e.g. stochastic) movements of the specimen (e.g. eye) can be used for improving the resolution and the contrast. For example, the saccadic movement of the specimen (e.g. an eye) may be in the order of 2 to 120 arcminutes. This rotation results in a lateral shift of the eye by 3.5 to 200 µm. This range is suitable for the application of the saccadic eye-movement to shift the illumination pattern relative to the fundus as described above.

In some embodiments, the relative position of the specimen with respect to the illumination pattern projected onto the specimen is constant during an acquisition cycle, whereas said relative position varies between the single images.

The method for non-invasive fluorescence observations of an eye fundus using an ophthalmoscope and the corresponding ophthalmoscope described above may be used for many applications in the field of ophthalmology. For example, diseases of the eye fundus (such as the age-related macular degeneration) can be detected by obtaining and evaluating a high resolution image.

The invention claimed is:

1. A method for non-invasive observations of a fundus using an ophthalmoscope (100), the method comprising:
   illuminating a retinal region of an eye (52) by projecting an illumination pattern of illumination light onto the retinal region of the eye (52);
   at least one of detecting at least a portion of fluorescent light emitted from the retinal region of the eye (52) and detecting at least a portion of illumination light reflected from the retinal region of the eye (52), thereby capturing a series of images of the retinal region of the eye (52) at a plurality of different relative positions of the retinal region of the eye (52) with respect to the illumination pattern projected onto the retinal region of the eye (52), wherein between the capturing of at least two images of the series the relative position of the retinal region of the eye (52) with respect to the illumination pattern projected onto the retinal region of the eye (52) is shifted in a non-controlled manner; and
   processing the captured images to extract a sub-resolution image of the retinal region of the eye (52).

2. The method according to claim 1, wherein the relative position of the retinal region of the eye (52) with respect to the illumination pattern projected onto the retinal region of the eye (52) is shifted in a non-controlled manner by utilizing at least one of stochastic saccades of the eye (52), stochastic stage scanning, and stochastic movement of a focusing lens system (42, 44) of an ophthalmoscope objective (40).

3. The method according to claim 1, wherein processing the captured images comprises:
   for each image of the series determining the non-controlled shift of the relative position of the retinal region of the eye (52) with respect to the illumination pattern projected onto the retinal region of the eye (52);
   a-posteriori shifting of each image of the series to reverse the determined shift of the relative position of the retinal region of the eye (52) with respect to the projected illumination pattern, thereby obtaining a corresponding shifted image; and
   processing the shifted images to extract a sub-resolution image of the retinal region of the eye (52).

4. The method according to claim 3, wherein determining the non-controlled shift of the relative position of the retinal region of the eye (52) with respect to the illumination pattern projected onto the retinal of the eye (52) comprises:
   applying an analytic deconvolution of each of a second and subsequent images of the series by a first image of the series to obtain a corresponding deconvolved image;
   determining the position of a maximum (P) of the analytic deconvolution of each of the deconvolved images; and
   determining the non-controlled shift of the relative position of the retinal region of the eye (52) with respect to the illumination pattern projected onto the retinal region of the eye (52) for each of the second and subsequent images of the series from the determined position of the maximum (P) of the analytic deconvolution.

5. The method according to claim 3, wherein determining of the non-controlled shift of the relative position of the retinal region of the eye (52) with respect to the illumination pattern projected onto the retinal of the eye (52) comprises:
   Fourier-transforming of each of the images of the series;
   dividing each of the Fourier-transformed second and each subsequent images by the Fourier-transformed first image to obtain a corresponding divided image;
   inverse Fourier-transforming each of the divided images;
   determining the position of a maximum (P) of intensity of each of the inverse Fourier-transformed divided images; and
   determining the non-controlled shift of the relative position of the retinal region of the eye (52) with respect to the illumination pattern projected onto the retinal of the eye (52) for each of the second and subsequent images of the series from the determined position of the maximum (P) of intensity of the inverse Fourier-transformed divided image.

6. The method according to claim 1, wherein the illumination pattern is projected onto the retinal region of the eye (52) through at least one objective (40) of the ophthalmoscope (100) having a numerical aperture of less than 0.5.

7. The method according to claim 1, wherein the retinal region of the eye (52) is illuminated only when images are captured.

8. The method according to claim 7, wherein the duration of on-times during which the retinal region of the eye (52) is illuminated is shorter than the duration of off-times during which the illumination of the retinal region of the eye (52) is interrupted.

9. The method according to claim 1, further comprising the steps of:

detecting non-controlled shifts of the relative position of the retinal region of the eye (52) with respect to the illumination pattern projected onto the retinal region of the eye (52); and synchronizing the illumination of the retinal region of the eye (52) and/or the capturing of a series of images with the detected non-controlled shifts of the relative position of the retinal region of the eye (52) with respect to the illumination pattern projected onto the retinal region of the eye (52).

10. The method according to claim 1, further comprising the sorting-out one or more of the captured images, wherein a particular image is sorted out if it is determined that the non-controlled shift of the relative position of the retinal region of the eye (52) with respect to the illumination pattern projected onto the retinal region of the eye (52) during the capturing of the image exceeds a predetermined threshold.

11. The method according to claim 1, further comprising:
focusing the illumination pattern of illumination light in a plurality of different focal planes;
for each focal plane obtaining a set of images including a plurality of images captured at a plurality of different relative positions of the retinal region of the eye (52) with respect to the illumination pattern projected onto the retinal region of the eye (52); and
generating a three-dimensional image based on the obtained sets of images for the plurality of different focal planes.

12. An ophthalmoscope (100) for non-invasive observations of a fundus, the ophthalmoscope (100) comprising:
a light source (10; 11; 12) configured to emit illumination light;
a pattern generation system (20; 22; 24) arranged in the optical path of the illumination light, said pattern generation system (20; 22; 24) configured to generate an illumination pattern of the illumination light;
at least one objective (40) arranged and configured to illuminate the retinal region of an eye (52) by projecting the illumination pattern onto the retinal region of the eye (52);
an image capturing system (70) configured to detect at least one of at least a portion of fluorescent light emitted from the retinal region of the eye (52) and at least a portion of illumination light reflected from the retinal region of the eye (52), thereby capturing a series of images of the retinal region of the eye (52) at a plurality of different relative positions of the retinal region of the eye (52) with respect to the illumination pattern projected onto the retinal region of the eye (52), wherein between the capturing of at least two images of the series the relative position of the retinal region of the eye (52) with respect to the illumination pattern projected onto the retinal region of the eye (52) is shifted in a non-controlled manner; and
a data processing system configured to process data obtained from the series of captured images, thereby producing a sub-resolution image of the retinal region of the eye (52).

13. The ophthalmoscope (100) according to claim 12, wherein the at least one objective (40) has a numerical aperture of less than 0.5.

14. The ophthalmoscope (100) according to claim 12, wherein the relative position of the retinal region of the eye (52) with respect to the illumination pattern projected onto the retinal region of the eye (52) is shifted in a non-controlled manner by utilizing at least one of stochastic saccades of the eye (52), stochastic stage scanning, and stochastic movement of a focusing lens system (42, 44) of the ophthalmoscope objective (40).

15. The ophthalmoscope (100) according to any claim 12, wherein the light source (10; 11; 12) is configured to emit stroboscopic illumination light having on- and off-times, wherein the retinal region of the eye (52) is illuminated only during the on-times, and wherein the on-times are respectively shorter than the off-times during which the illumination of the retinal region of the eye (52) is interrupted.

16. The ophthalmoscope (100) according to claim 12, further comprising:
a shift detector for detecting non-controlled shifts of the relative position of the retinal region of the eye (52) with respect to the illumination pattern projected onto the retinal region of the eye (52); and
a synchronizer configured to synchronize at least one of the illumination of the retinal region of the eye (52) and the capturing of a series of raw images with the detected non-controlled shifts of the relative position of the retinal region of the eye (52) with respect to the illumination pattern projected onto the retinal region of the eye (52).

17. The ophthalmoscope (100) according to claim 12, wherein the pattern generation system (20; 22; 24) comprises an intensity modulating light transmitting spatial light modulator.

18. A computer implemented method for generating sub-resolution images of a fundus based on a series of images of the retinal region of the eye (52) obtained by an ophthalmoscope (100), wherein the series of images is obtained by projecting an illumination pattern of illumination light onto the retinal region of the eye (52), thereby illuminating the retinal region of the eye 52 and at least one of detecting at least a portion of fluorescent light emitted from the retinal region of the eye (52) and detecting at least a portion of illumination light reflected from the retinal region of the eye (52), thereby capturing a series of images at a plurality of different relative positions of the retinal region of the eye (52) with respect to the illumination pattern projected onto the retinal region of the eye (52), wherein between the capturing of at least two images of the series the relative position of the retinal region of the eye (52) with respect to the illumination pattern projected onto the retinal region of the eye (52) is shifted in a non-controlled manner, said method comprising:
receiving the series of images of the retinal region of the eye (52);
for each received image determining the non-controlled shift of the relative position of the retinal region of the eye (52) with respect to the illumination pattern projected onto the retinal region of the eye (52);
a-posteriori shifting of each received image to reverse the corresponding non-controlled shift of the retinal region of the eye (52) with respect to the projected illumination pattern, thereby obtaining a corresponding shifted image; and
processing the shifted images to extract a sub-resolution image.

19. A computer program product, which, when loaded into the memory of a computer and executed by the computer performs a computer implemented method according to claim 18.

* * * * *